United States Patent
McKinnell et al.

(10) Patent No.: US 7,662,815 B2
(45) Date of Patent: Feb. 16, 2010

(54) DIARYL ETHER $\beta_2$ ADRENERGIC RECEPTOR AGONISTS

(75) Inventors: Robert Murray McKinnell, Half Moon Bay, CA (US); Edmund J. Moran, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 179 days.

(21) Appl. No.: 11/985,987

(22) Filed: Nov. 19, 2007

(65) Prior Publication Data

US 2008/0113981 A1 May 15, 2008

Related U.S. Application Data

(62) Division of application No. 11/185,295, filed on Jul. 20, 2005, now Pat. No. 7,317,023.

(60) Provisional application No. 60/589,728, filed on Jul. 21, 2004.

(51) Int. Cl.
*A61K 31/4704* (2006.01)
*A61K 31/4725* (2006.01)
*A61K 31/5377* (2006.01)

(52) U.S. Cl. .................. 514/235.5; 514/312; 514/314; 514/651

(58) Field of Classification Search .............. 514/312, 514/314, 235.5, 651
See application file for complete search history.

(56) References Cited

U.S. PATENT DOCUMENTS

| | | | |
|---|---|---|---|
| 4,894,219 A | 1/1990 | Baker et al. | |
| 4,992,474 A | 2/1991 | Skidmore et al. | |
| 5,064,863 A | 11/1991 | Alig et al. | |
| 5,977,154 A | 11/1999 | Bell et al. | |
| 6,346,532 B1 | 2/2002 | Maruyama et al. | |
| 6,436,914 B1 | 8/2002 | Sher et al. | |
| 6,541,669 B1 | 4/2003 | Moran et al. | |
| 6,576,793 B1 | 6/2003 | Moran et al. | |
| 6,653,323 B2 | 11/2003 | Moran et al. | |
| 6,670,376 B1 | 12/2003 | Moran et al. | |
| 6,949,568 B2 | 9/2005 | Moran et al. | |
| 7,037,938 B2 | 5/2006 | Hattori et al. | |
| 7,125,892 B2 | 10/2006 | Moran et al. | |
| 7,399,863 B2 | 7/2008 | Linsell et al. | |
| 7,402,673 B2 | 7/2008 | Linsell | |
| 2002/0022625 A1 | 2/2002 | Walland et al. | |
| 2002/0143034 A1 | 10/2002 | Taniguchi et al. | |
| 2003/0229058 A1 | 12/2003 | Moran et al. | |
| 2004/0242890 A1 | 12/2004 | Coe et al. | |
| 2005/0159448 A1 | 7/2005 | McKinnell et al. | |

2008/0039495 A1 2/2008 Linsell

FOREIGN PATENT DOCUMENTS

| | | |
|---|---|---|
| EP | 0 147 719 A2 | 7/1985 |
| GB | 1 463 219 | 2/1977 |
| WO | WO 00/40560 | 7/2000 |
| WO | WO 01/07026 A2 | 2/2001 |
| WO | WO 01/35947 A2 | 5/2001 |
| WO | WO 01/36413 A1 | 5/2001 |
| WO | WO 01/42193 A1 | 6/2001 |
| WO | WO 02/00622 A2 | 1/2002 |
| WO | WO 02/06276 A1 | 1/2002 |
| WO | WO 02/38544 A2 | 5/2002 |
| WO | WO 03/024439 A1 | 3/2003 |
| WO | WO 2004/002939 A2 | 1/2004 |
| WO | WO 2004/016578 A2 | 2/2004 |
| WO | WO 2004/016601 A1 | 2/2004 |
| WO | WO 2004016601 A1 * | 2/2004 |

OTHER PUBLICATIONS

Bompart et al., "Synthesis of new β-blockers analogs of bevantolol", Annales Pharmaceutiques Francaises, Volume Date 1984, 42(6), pp. 537-545 (1985) (In French with English abstract).
Bompart et al., "Synthesis of new β-blockers analogous of the bevantolol or the alprenolol", Annales Pharmaceutiques Francaises, Volume Date 1987, 45(5), pp. 379-387 (1988) (In French with English abstract).
Deyrup et al., "Structure-affinity profile of 8-hydroxycarbostyril-based agonists that dissociate slowly from the Beta2-adrenoceptor", Naunyn-Schmiedeberg's Arch Pharmacol (1999) 359:168-177.
Fotsch et al., "Synthesis and Structure-Activity Relationships of Trisubstituted Phenyl Urea Derivatives as NeuropeptideY5 Receptor antagonists", J. Med. Chem., (2001), 44:2344-2356.
Isogaya et al., "Binding Pockets of the $\beta_1$- and $\beta_2$-Adrenergic Receptors for Subtype-Selective Agonists", Molecular Pharmacology, vol. 56, pp. 875-885 (1999).
Milecki et al., "Carbostyril Derivatives Having Potent β-Adrenergic Agonist Properties", J. Med. Chem, (1987), 30, 1563-1566.
Shuker et al., "The Application of High-Throughput Synthesis and Purification to the Preparation of Ethanolamines", Tetrahedron Letters, (1997), 38(35):6149-6152.
Yokoi et al., "The Development of a Radioimmunoassay for Formoterol", Life Sciences, (1983) vol. 33, No. 17, pp. 1665-1672.
Yoshizaki et al., "Sympathomimetic Amines Having a Carbostyril Nucleus", J. Med. Chem., (1976), vol. 19, No. 9, pp. 1138-1142.
Alikhani et al., "Long-chain formoterol analogues: an investigation into the effect of Increasing amino-substituent chain length on the β2-adrenoceptor activity", Bioorganic & Medicinal Chemistry Letters, 14, pp. 4705-4710 (2004).

* cited by examiner

*Primary Examiner*—Yong Chu
(74) *Attorney, Agent, or Firm*—Jeffrey A. Hagenah; Roberta P. Saxon

(57) ABSTRACT

The invention provides novel $\beta_2$ adrenergic receptor agonist compounds. The invention also provides pharmaceutical compositions comprising such compounds, methods of using such compounds to treat diseases associated with $\beta_2$ adrenergic receptor activity, and processes and intermediates useful for preparing such compounds.

16 Claims, No Drawings

DIARYL ETHER β₂ ADRENERGIC RECEPTOR AGONISTS

CROSS-REFERENCE TO RELATED APPLICATIONS

This application is divisional of U.S. application Ser. No. 11/185,295, filed Jul. 20, 2005 now U.S. Pat. No. 7,317,023; which claims the benefit of U.S. Provisional Application No. 60/589,728, filed on Jul. 21, 2004; the entire disclosures of which are ncorporated herein by reference in their entirety.

FIELD OF THE INVENTION

The invention is directed to novel $\beta_2$ adrenergic receptor agonists. The invention is also directed to pharmaceutical compositions comprising such compounds, methods of using such compounds to treat diseases associated with $\beta_2$ adrenergic receptor activity, and processes and intermediates useful for preparing such compounds.

BACKGROUND OF THE INVENTION $\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also useful for treating pre-term labor, and are potentially useful for treating neurological disorders and cardiac disorders. In spite of the success that has been achieved with certain $\beta_2$ adrenergic receptor agonists, current agents possess less than desirable duration of action, potency, selectivity, and/or onset. Thus, there is a need for new $\beta_2$ adrenergic receptor agonists having improved properties, such as improved duration of action, potency, selectivity, and/or onset.

SUMMARY OF THE INVENTION

The invention provides novel compounds that possess $\beta_2$ adrenergic receptor agonist activity. Among other properties, compounds of the invention are potent and selective $\beta_2$ adrenergic receptor agonists.

Accordingly, this invention provides a compound of formula (I):

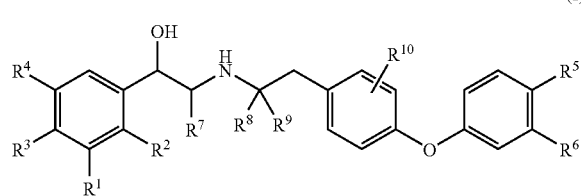

(I)

wherein:
each of $R^1$, $R^2$, $R^3$, and $R^4$ is independently selected from hydrogen, hydroxy, amino, halo, —CH₂OH and —NHCHO, or $R^1$ and $R^2$ taken together are selected from —NHC(=O)CH=CH—, —CH=CHC(=O)NH—, —NHC(=O)S—, and —SC(=O)NH—;

$R^5$ and $R^6$ are independently selected from hydrogen, hydroxy, halo, $C_{1-6}$alkoxy, $C_{1-6}$alkyl, —$C_{1-6}$alkylenyl-NR$^a$R$^b$, —O—$C_{1-6}$alkylenyl-NR$^a$R$^b$; —O—$C_{1-4}$alkylenyl-O—$C_{1-4}$alkylenyl-NR$^a$R$^b$, —SO₂NR$^a$R$^b$, —NR$^c$R$^d$, phenyl, and heteroaryl; provided that $R^5$ and $R^6$ are not both hydrogen; wherein each phenyl is optionally substituted with 1 or 2 substituents selected from R$^f$; each heteroaryl is optionally substituted with 1 or 2 substituents selected from R$^g$; and each $C_{1-6}$alkyl is optionally substituted with 1 to 3 substituents selected from halo, hydroxy, $C_{1-6}$alkoxy, and amino;

$R^7$ is hydrogen or $C_{1-6}$alkyl;
$R^8$ is hydrogen or $C_{1-6}$alkyl;
$R^9$ is hydrogen or $C_{1-6}$alkyl;
$R^{10}$ is selected from hydrogen, halo, hydroxy, $C_{1-6}$alkyl, $C_{2-6}$alkenyl, $C_{2-6}$alkynyl, $C_{1-6}$alkoxy, aryl, heteroaryl, cycloalkyl, and heterocyclyl; or $R^9$ together with $R^{10}$ is —CH₂— or —CH₂CH₂—;

$R^a$, $R^b$, $R^c$, $R^d$, and $R^e$ are each independently hydrogen or $C_{1-6}$ alkyl, wherein each $C_{1-6}$alkyl is optionally substituted with 1 to 3 substituents selected from hydroxy, $C_{1-6}$alkoxy, and amino; or $R^a$ and $R^b$, or $R^c$ and $R^d$ together with the nitrogen atom to which they are attached form a heteroaryl or heterocyclic ring having from 4 to 7 ring atoms, and containing 1 to 3 heteroatoms selected from nitrogen, oxygen, and sulfur;

$R^f$ is selected from hydroxy, halo, $C_{1-6}$alkoxy, $C_{1-6}$alkyl, $C_{2-6}$alkenyl, $C_{2-6}$alkynyl, —C(=O)OH, —CN, —NO₂, —C(=O)R$^e$, —SO₂—$C_{1-6}$alkyl, —$C_{1-6}$alkylenyl-NR$^a$R$^b$, and —C(=O)NR$^a$R$^b$, wherein each $C_{1-6}$alkyl is optionally substituted with 1 to 3 substituents selected from halo, hydroxy, $C_{1-6}$alkoxy, and amino; and $R^g$ is $C_{1-6}$alkyl or oxo, wherein each $C_{1-6}$alkyl is optionally substituted with 1 to 3 substituents selected from halo, hydroxy, $C_{1-6}$alkoxy, and amino;

or a pharmaceutically-acceptable salt or solvate or stereoisomer thereof.

The invention also provides a pharmaceutical composition comprising a a pharmaceutically-acceptable carrier and a therapeutically effective amount of a compound of formula (I) or a pharmaceutically-acceptable salt or solvate or stereoisomer thereof. The pharmaceutical compositions of the invention optionally further comprises a therapeutically effective amount of one or more other therapeutic agents. Suitable additional agents include anti-inflammatory agents (e.g., corticosteroids and non-steroidal anti-inflammatory agents (NSAIDs)), anticholinergic agents (particularly muscarinic receptor antagonists), other $\beta_2$ adrenergic receptor agonists, antiinfective agents (e.g., antibiotics or antiviral), antihistamines, and a phosphodiesterase 4 (PDE4) inhibitor.

The invention further provides combinations comprising a compound of the invention and one or more other therapeutic agents and pharmaceutical compositions comprising such combinations and a pharmaceutically-acceptable carrier.

The invention also provides a method of treating a mammal having a disease or condition associated with $\beta_2$ adrenergic receptor activity, (e.g. a pulmonary disease, such as asthma or chronic obstructive pulmonary disease, pre-term labor, a neurological disorder, a cardiac disorder, or inflammation), the method comprising administering to the mammal, a therapeutically effective amount of a compound of formula (I) or a pharmaceutically-acceptable salt or solvate or stereoisomer thereof. The invention further provides a method of treatment comprising administering a therapeutically effective amount of a compound of the invention with a therapeutically effective amount of one or more other therapeutic agents.

The invention also provides a method of treating a mammal having a disease or condition associated with $\beta_2$ adrenergic receptor activity, the method comprising administering to the mammal, a therapeutically effective amount of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically-acceptable salt or solvate or stereoisomer thereof, as a research tool for studying a biological system or sample or for discovering new $\beta_2$ adrenergic receptor agonists.

In separate and distinct aspects, the invention also provides synthetic processes and novel intermediates, including compounds of formula (III) and (IV) described herein, which are useful for preparing compounds of the invention.

The invention also provides a compound of the invention as described herein for use in medical therapy, as well as the use of a compound of the invention in the manufacture of a formulation or medicament for treating a mammal having a disease or condition associated with $\beta_2$ adrenergic receptor activity, (e.g. a pulmonary disease, such as asthma or chronic obstructive pulmonary disease, pre-term labor, a neurological disorder, a cardiac disorder, or inflammation).

DETAILED DESCRIPTION OF THE INVENTION

The invention provides novel diaryl ether $\beta_2$ adrenergic receptor agonists of formula (I), or pharmaceutically-acceptable salts or solvates or stereoisomers thereof. The following substituents and values are intended to provide representative examples of various aspects of the invention. These representative values are intended to further define such aspects and are not intended to exclude other values or limit the scope of the invention.

In specific aspects of the invention, $R^1$ is halo, —$CH_2OH$, or —NHCHO; or $R^1$ is chloro, —$CH_2OH$, or —NHCHO.

In another specific aspect, $R^1$ is —$CH_2OH$ or —NHCHO.

In a specific aspect, $R^2$ is hydrogen.

In a specific aspect, $R^1$ and $R^2$ taken together are —NHC(=O)CH=CH—, —CH=CHC(=O)NH—, —NHC(=O)S—; or —SC(=O)NH—.

In another specific aspect, $R^1$ and $R^2$ taken together are —NHC(=O)CH=CH— or —CH=CHC(=O)NH—.

In a specific aspect, $R^1$ is —$CH_2OH$ or —NHCHO, and $R^2$ is hydrogen; or $R^1$ and $R^2$ taken together are —NHC(=O)CH=CH—, —CH=CHC(=O)NH—, —NHC(=O)S—, or —SC(=O)NH—.

In a specific aspect, $R^3$ is hydroxy or amino.

In another specific aspect, $R^3$ is hydroxy.

In specific aspects, $R^4$ is hydrogen or halo; or $R^4$ is hydrogen or chloro. In another specific aspect, $R^4$ is hydrogen.

In a specific aspect, $R^1$ is —NHCHO, $R^3$ is hydroxy, and $R^2$ and $R^4$ are each hydrogen.

In another specific aspect, $R^1$ is —$CH_2OH$, $R^3$ is hydroxy, and $R^2$ and $R^4$ are each hydrogen.

In another specific aspect, $R^1$ and $R^2$ taken together are —NHC(=O)CH=CH— or —CH=CHC(=O)NH—, $R^3$ is hydroxy, and $R^4$ is hydrogen.

In another specific aspect, $R^1$ and $R^2$ taken together are —NHC(=O)S— or —SC(=O)NH—; $R^3$ is hydroxy, and $R^4$ is hydrogen.

In yet another specific aspect, $R^1$ and $R^4$ are chloro, $R^3$ is amino, and $R^2$ is hydrogen.

In a specific aspect, $R^5$ is selected from hydrogen, hydroxy, $C_{1-6}$alkoxy, $C_{1-6}$alkyl, —$C_{1-6}$alkylenyl-$NR^aR^b$, —O—$C_{1-6}$alkylenyl-$NR^aR^b$, —$SO_2NR^aR^b$, and $NR^cR^d$, wherein each $C_{1-6}$alkyl is optionally substituted with 1 to 3 substituents selected from halo, hydroxy, $C_{1-6}$alkoxy, and amino.

In another specific aspect, $R^5$ is selected from hydrogen, hydroxy, $C_{1-3}$alkoxy, $C_{1-4}$alkyl, —$C_{1-4}$alkylenyl-$NR^aR^b$, —O—$C_{1-4}$alkylenyl-$NR^aR^b$, —$SO_2NR^aR^b$, and —$NR^cR^d$.

In yet another specific aspect, $R^5$ is selected from hydrogen, hydroxy, methoxy, ethoxy, methyl, ethyl, —$(CH_2)_2NH_2$, —$(CH_2)_3NH_2$, —$CH_2C(CH_3)_2NH_2$, —$(CH_2)_2N(CH_3)_2$, —$O(CH_2)_2NH_2$, —$O(CH_2)_3NH_2$, —$OCH_2C(CH_3)_2NH_2$, —$O(CH_2)_4NH_2$, 4-morpholinylethoxy, and 4-piperazinylethoxy.

In a specific aspect, $R^6$ is heteroaryl, optionally substituted with 1 or 2 substituents selected from $R^g$. In another specific aspect, $R^6$ is furyl, thienyl, pyrrolyl, or pyridyl, optionally substituted with 1 or 2 methyl substituents.

In another specific aspect, $R^6$ is phenyl, optionally substituted with 1 or 2 substituents selected from $R^f$.

In another specific aspect, $R^6$ is hydrogen.

In yet another specific aspect, $R^6$ is —$(CH_2)_2NH_2$, —$(CH_2)_3NH_2$, —$CH_2C(CH_3)_2NH_2$, or —$(CH_2)_2N(CH_3)_2$.

In a specific aspect of the invention, $R^5$ and $R^6$ are each independently selected from hydrogen, hydroxy, $C_{1-6}$alkoxy, $C_{1-6}$alkyl, —$C_{1-6}$alkenyl-$NR^aR^b$, —O—$C_{1-6}$alkylenyl-$NR^aR^b$; —$NR^cR^d$, phenyl, and heteroaryl; provided that $R^5$ and $R^6$ are not both hydrogen; wherein each phenyl is optionally substituted with 1 or 2 substituents selected from $R^f$; each heteroaryl is optionally substituted with 1 or 2 substituents selected from $R^g$; and each $C_{1-6}$alkyl is optionally substituted with 1 to 3 substituents selected from halo, hydroxy, $C_{1-6}$alkoxy, and amino.

In another aspect, $R^5$ and $R^6$ are each independently selected from hydrogen, hydroxy, $C_{1-6}$alkoxy, $C_{1-6}$alkyl, —$C_{1-6}$alkylenyl-$NR^aR^b$, —O—$C_{1-6}$alkylenyl-$NR^aR^b$, and —$NR^cR^d$; provided that $R^5$ and $R^6$ are not both hydrogen; wherein each $C_{1-6}$alkyl is optionally substituted with 1 to 3 substituents selected from halo, hydroxy, $C_{1-6}$alkoxy, and amino.

In another specific aspect, one of $R^5$ and $R^6$ is selected from furyl, thienyl, pyrrolyl, and pyridyl; wherein furyl, thienyl, pyrrolyl, and pyridyl are optionally substituted with 1 or 2 methyl substituents; and the other of $R^5$ and $R^6$ is hydrogen or $C_{1-6}$alkoxy.

In yet another aspect, $R^5$ and $R^6$ are each independently selected from hydrogen, hydroxy, methoxy, ethoxy, methyl, ethyl, —$CF_3$, —$O(CH_2)_2NH_2$, —$O(CH_2)_3NH_2$, —$OCH_2C(CH_3)_2NH_2$, —$O(CH_2)_4NH_2$, —$(CH_2)_2NH_2$, —$(CH_2)_3NH_2$, —$CH_2C(CH_3)_2NH_2$, —$(CH_2)_2N(CH_3)_2$, 4-morpholinylethoxy, 4-piperazinylethoxy, phenyl, furyl, thienyl, pyrrolyl, and pyridyl; provided that $R^5$ and $R^6$ are not both hydrogen; wherein each phenyl is optionally substituted with 1 or 2 substituents selected from $R^f$, and each furyl, thienyl, pyrrolyl, and pyridyl is optionally substituted with 1 or 2 substituents selected from $R^g$.

In another aspect, one of $R^5$ and $R^6$ is selected from —$O(CH_2)_2NH_2$, —$O(CH_2)_3NH_2$, —$OCH_2C(CH_3)_2NH_2$, —$O(CH_2)_4NH_2$, —$(CH_2)_2NH_2$, —$(CH_2)_3NH_2$, —$CH_2C(CH_3)_2NH_2$, —$(CH_2)_2N(CH_3)_2$, 4-morpholinylethoxy, and 4-piperazinylethoxy; and the other of $R^5$ and $R^6$ is selected from hydrogen, methoxy, ethoxy, —$CF_3$, and methyl.

In another specific aspect, $R^5$ is selected from —$O(CH_2)_2NH_2$, —$O(CH_2)_3NH_2$, —$OCH_2C(CH_3)_2NH_2$, —$O(CH_2)_4NH_2$, —$(CH_2)_2NH_2$, —$(CH_2)_3NH_2$, —$CH_2C(CH_3)_2NH_2$, —$(CH_2)_2N(CH_3)_2$, 4-morpholinylethoxy, and 4-piperazinylethoxy; and $R^6$ is hydrogen, methoxy, ethoxy, —$CF_3$, and methyl.

In another specific aspect, $R^5$ is hydrogen; and $R^6$ is selected from —$(CH_2)_2NH_2$, —$(CH_2)_3NH_2$, —$CH_2C(CH_3)_2NH_2$, and —$(CH_2)_2N(CH_3)_2$.

In still another specific aspect, $R^5$ is selected from hydrogen, hydroxy, $C_{1-6}$alkoxy, $C_{1-6}$alkyl, —$C_{1-6}$alkylenyl-$NR^aR^b$, and —O—$C_{1-6}$alkylenyl-$NR^aR^b$; wherein each $C_{1-6}$alkyl is optionally substituted with 1 to 3 substituents selected from halo, hydroxy, $C_{1-6}$alkoxy, and amino; and $R^6$ is selected from phenyl optionally substituted with 1 or 2 substituents selected from $R^f$; and heteroaryl, optionally substituted with 1 or 2 substituents selected from $R^g$. Within this group of compounds, a specific value for $R^6$ is phenyl optionally substituted with 1 or 2 substituents selected from $R^f$.

In another specific aspect, $R^5$ is selected from hydrogen, hydroxy, methoxy, ethoxy, methyl, and ethyl; and $R^6$ is selected from phenyl, furyl, thienyl, pyrrolyl, and pyridyl; wherein phenyl is optionally substituted with 1 or 2 substituents selected from $R^f$, and furyl, thienyl, pyrrolyl, and pyridyl are optionally substituted with 1 or 2 substituents selected from R. For example, $R^5$ is selected from hydrogen, methoxy, and ethoxy, and $R^6$ is phenyl optionally substituted with 1 or 2 substituents selected from $R^f$.

In a specific aspect, $R^7$ is hydrogen or $C_{1-3}$alkyl. In another specific aspect, $R^7$ is hydrogen.

In a specific aspect, $R^8$ is hydrogen or $C_{1-3}$alkyl. In another specific aspect, $R^8$ is hydrogen.

In a specific aspect, $R^9$ is hydrogen or $C_{1-3}$alkyl, such as methyl. In another specific aspect, $R^9$ is hydrogen.

In a specific aspect, when $R^{10}$ is at the 3 position of the phenyl ring relative to the oxygen atom to which the phenyl ring is attached, $R^9$ together with $R^{10}$ is —$CH_2$— or —$CH_2CH_2$—.

In a specific aspect, $R^{10}$ is hydrogen, chloro, bromo, $C_{1-4}$alkyl, $C_{1-4}$alkoxy, or $R^9$ together with $R^{10}$ is —$CH_2$— or —$CH_2CH_2$—.

In another specific aspect, $R^{10}$ is hydrogen.

In a specific aspect, each of $R^4$, $R^7$, $R^8$, $R^9$, and $R^{10}$ are hydrogen.

In a specific aspect, $R^a$, $R^b$, $R^c$, $R^d$, and $R^e$ are each independently hydrogen or $C_{1-4}$alkyl, wherein each $C_{1-4}$alkyl is optionally substituted with 1 to 3 substituents selected from hydroxy, $C_{1-6}$alkoxy, and amino.

In another specific aspect, $R^a$ and $R^b$, or $R^c$ and $R^d$ together with the nitrogen atom to which they are attached form a heteroaryl or heterocyclic ring having from 4 to 7 ring atoms, and containing 1 to 3 heteroatoms selected from nitrogen, oxygen, and sulfur.

In yet another specific aspect, $R^a$, $R^b$, $R^c$, $R^d$, and $R^e$ are each independently hydrogen, methyl or ethyl; or $R^a$ and $R^b$, or $R^c$ and $R^d$ together with the nitrogen atom to which they are attached form piperidine, piperazine, morpholine, pyrrolidine or pyridine.

In a specific aspect, $R^f$ is selected from hydroxy, halo, $C_{1-6}$alkoxy, $C_{1-6}$alkyl, —C(=O)OH, —CN, —$NO_2$, —C(=O)$R^e$, —$C_{1-6}$alkylenyl-$NR^aR^b$, and —C(=O)$NR^aR^b$; wherein each $C_{1-6}$alkyl is optionally substituted with 1 to 3 substituents selected from halo, hydroxy, $C_{1-6}$alkoxy, and amino.

In another specific aspect, $R^f$ is selected from hydroxy, chloro, fluoro, methoxy, ethoxy, methyl, ethyl, isopropyl, hydroxymethyl, —C(=O)OH, —C(=O)H, —C(=O)$CH_3$, —CN, —$NO_2$, —$CH_2NH_2$, —$CH_2N(CH_3)_2$, —$CH_2NHCH(CH_3)_2$, —$C(CH_3)_2NH_2$, —$(CH_2)_2NH_2$, 4-morpholinylethyl, 4-piperazinylmethyl, 1-piperidinylmethyl, and —C(=O)$NH_2$.

In a specific aspect, $R^g$ is $C_{1-4}$alkyl or oxo, wherein each $C_{1-4}$alkyl is optionally substituted with 1 to 3 substituents selected from halo, hydroxy, $C_{1-4}$alkoxy, and amino.

In another specific aspect, $R^g$ is methyl or oxo. In yet another specific aspect, $R^g$ is methyl.

In one aspect, the invention provides a compound of formula (II):

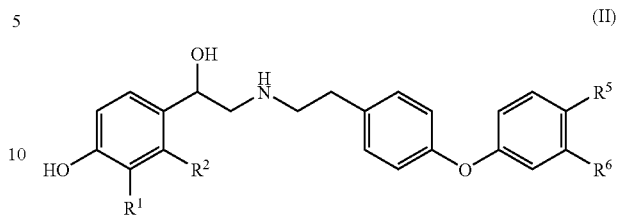

(II)

wherein:

$R^1$ is —$CH_2OH$ or —NHCHO, and $R^2$ is hydrogen; or $R^1$ and $R^2$ taken together are —NHC(=O)CH=CH—, —CH=CHC(=O)NH—, —NHC(=O)S—, or —SC(=O)NH—; and $R^5$ and $R^6$ are as defined herein.

In another aspect, the invention provides a compound of formula (II) wherein:

$R^5$ and $R^6$ are each independently selected from hydrogen, hydroxy, $C_{1-6}$alkoxy, $C_{1-6}$alkyl, —$C_{1-6}$alkylenyl-$NR^aR^b$, —O—$C_{1-6}$alkylenyl-$NR^aR^b$; —$NR^cR^d$, phenyl, and heteroaryl; provided that $R^5$ and $R^6$ are not both hydrogen; wherein each phenyl is optionally substituted with 1 or 2 substituents selected from $R^f$; each heteroaryl is optionally substituted with 1 or 2 substituents selected from $R^g$; and each heteroaryl is optionally substituted with 1 to 3 substituents selected from halo, hydroxy, $C_{1-6}$alkoxy, and amino;

$R^a$, $R^b$, $R^c$, $R^d$, and $R^e$ are each independently hydrogen or $C_{1-6}$alkyl, wherein each $C_{1-6}$alkyl is optionally substituted with 1 to 3 substituents selected from hydroxy, $C_{1-6}$alkoxy, and amino; or $R^a$ and $R^b$, or $R^c$ and $R^d$ together with the nitrogen atom to which they are attached form a heteroaryl or heterocyclic ring having from 4 to 7 ring atoms, and containing 1 to 3 heteroatoms selected from nitrogen, oxygen, and sulfur;

$R^f$ is selected from hydroxy, halo, $C_{1-6}$alkoxy, $C_{1-6}$alkyl, —C(=O)OH, —CN, —$NO_2$, —C(=O)$R^e$, —$C_{1-6}$alkylenyl-$NR^aR^b$, and —C(=O)$NR^aR^b$; wherein each $C_{1-6}$alkyl is optionally substituted with 1 to 3 substituents selected from halo, hydroxy, $C_{1-6}$alkoxy, and amino; and $R^g$ is selected from $C_{1-6}$alkyl, wherein each $C_{1-6}$alkyl is optionally substituted with 1 to 3 substituents selected from halo, hydroxy, $C_{1-6}$alkoxy, and amino;

or a pharmaceutically-acceptable salt or solvate or stereoisomer thereof.

A specific group of compounds within this aspect is the group of compounds of formula (II) wherein $R^1$ is —$CH_2OH$, and $R^2$ is hydrogen.

Another specific group of compounds within this aspect is the group of compounds of formula (II) wherein $R^1$ is —NHCHO, and $R^2$ is hydrogen.

Yet another specific group of compounds within this aspect is the group of compounds of formula (II) wherein $R^1$ and $R^2$ taken together are —NHC(=O)CH=CH— or —CH=CHC(=O)NH—.

Yet another specific group of compounds of formula (II) is the group wherein $R^1$ and $R^2$ taken together are —NHC(=O)CH=CH—, or —CH=CHC(=O)NH—; $R^5$ is hydrogen, methoxy or ethoxy; and $R^6$ is phenyl optionally substituted with 1 or 2 substituents selected from $R^f$.

Particular mention may be made of the following compounds:

8-hydroxy-5-((R)-1-hydroxy-2-{2-[4-(6-methoxybiphe-nyl-3-yloxy)phenyl]-ethylamino}ethyl)-1H-quinolin-2-one;
5-((R)-2-{2-[4-(biphenyl-3-yloxy)phenyl]ethylamino}-1-hydroxyethyl)-8-hydroxy-1H-quinolin-2-one;
5-[(R)-2-(2-{4-[4-(2-amino-2-methylpropoxy)phenoxy]phenyl}ethyl-amino)-1-hydroxyethyl]-8-hydroxy-1H-quinolin-2-one;
5-[(R)-2-(2-{4-[3-(3-aminopropyl)-4-methoxyphenoxy]phenyl}ethyl-amino)-1-hydroxyethyl]-8-hydroxy-1H-quinolin-2-one;
5-[(R)-2-(2-{4-[4-(2-aminoethoxy)-3-trifluoromethylphenoxy]phenyl}-ethylamino)-1-hydroxyethyl]-8-hydroxy-1H-quinolin-2-one;
5-[(R)-2-(2-{4-[4-(3-aminopropoxy)phenoxy]phenyl}ethylamino)-1-hydroxyethyl]-8-hydroxy-1H-quinolin-2-one;
5-{(R)-2-[2-(4-{4-[2-(2-aminoethoxy)ethoxy]phenoxy}phenyl)ethyl-amino]-1-hydroxyethyl}-8-hydroxy-1H-quinolin-2-one;
8-hydroxy-5-[(R)-1-hydroxy-2-(2-{4-[4-(2-morpholin-4-ylethoxy)-phenoxy]phenyl}ethylamino)ethyl]-1H-quinolin-2-one;
8-hydroxy-5-[(R)-1-hydroxy-2-(2-{4-[4-(2-piperazin-1-ylethoxy)phenoxy]-phenyl}ethylamino)ethyl]-1H-quinolin-2-one;
5-[(R)-2-(2-{4-[3-(2-dimethylaminoethyl)-4-methoxyphenoxy]phenyl}-ethylamino)-1-hydroxyethyl]-8-hydroxy-1H-quinolin-2-one;
5-((R)-2-{2-[4-(4'-chlorobiphenyl-3-yloxy)phenyl]ethylamino}-1-hydroxyethyl)-8-hydroxy-1H-quinolin-2-one;
8-hydroxy-5-((R)-1-hydroxy-2-{2-[4-(4'-methoxybiphenyl-3-yloxy)phenyl]ethylamino}ethyl)-1H-quinolin-2-one;
3'-(4-{2-[(R)-2-hydroxy-2-(8-hydroxy-2-oxo-1,2-dihydro-quinolin-5-yl)ethylamino]ethyl}phenoxy)biphenyl-3-carbonitrile;
8-hydroxy-5-((R)-1-hydroxy-2-{2-[4-(4-morpholin-4-yl-phenoxy)-phenyl]ethylamino}ethyl)-1H-quinolin-2-one;
5-[(R)-2-(2-{4-[3'-(2-aminoethyl)-6-methoxybiphenyl-3-yloxy]phenyl}-ethylamino)-1-hydroxyethyl]-8-hydroxy-1H-quinolin-2-one;
8-hydroxy-5-((R)-1-hydroxy-2-{2-[4-(6-methoxy-3'-morpholin-4-ylmethylbiphenyl-3-yloxy)phenyl]ethylamino}ethyl)-1H-quinolin-2-one;
N-[5-((R)-2-{2-[4-(biphenyl-3-yloxy)phenyl]ethylamino}-1-hydroxyethyl)-2-hydroxyphenyl]formamide;
N-{5-[(R)-2-(2-{4-[4-(2-aminoethoxy)phenoxy]phenyl}ethylamino)-1-hydroxyethyl]-2-hydroxyphenyl}formamide;
N-{5-[(R)-2-(2-{4-[3-(2-dimethylaminoethyl)-4-methoxyphenoxy]phenyl}-ethylamino)-1-hydroxyethyl]-2-hydroxyphenyl}formamide;
4-((R)-2-{2-[4-(biphenyl-3-yloxy)phenyl]ethylamino}-1-hydroxyethyl)-2-hydroxymethylphenol;
4-((R)-2-{2-[4-(2'-amino-3'-ethyl-6-methoxybiphenyl-3-yloxy)phenyl]-ethylamino}-1-hydroxyethyl)-2-hydroxymethylphenol;
2-hydroxymethyl-4-((R)-1-hydroxy-2-{2-[4-(4-morpholin-4-ylphenoxy)phenyl]ethylamino}ethyl)phenol;

where the chemical nomenclature conforms to that of the automatic naming program AutoNom, as provided by MDL Information Systems, GmbH (Frankfurt, Germany).

Particular mention may also be made of the following compounds:
5-(2-{2-[4-(3'-chloro-6-methoxybiphenyl-3-yloxy)phenyl]ethylamino}-1-hydroxyethyl)-8-hydroxy-1H-quinolin-2-one;
5'-(4-{2-[2-hydroxy-2-(8-hydroxy-2-oxo-1,2-dihydro-quinolin-5-yl)ethyl-amino]ethyl}phenoxy)-2'-methoxybiphenyl-3-carbonitrile;
5-(2-{2-[4-(3'-aminomethyl-6-methoxybiphenyl-3-yloxy)phenyl]ethyl-amino}-1-hydroxyethyl)-8-hydroxy-1H-quinolin-2-one;
5-(2-{2-[4-(4'-aminomethyl-6-methoxybiphenyl-3-yloxy)phenyl]ethyl-amino}-1-hydroxyethyl)-8-hydroxy-1H-quinolin-2-one;
N-[5-(2-{2-[4-(3'-chloro-6-methoxybiphenyl-3-yloxy)phenyl]ethyl-amino}-1-hydroxyethyl)-2-hydroxyphenyl]formamide;
N-[5-(2-{2-[4-(3'-cyano-6-methoxybiphenyl-3-yloxy)phenyl]ethyl-amino}-1-hydroxyethyl)-2-hydroxyphenyl]formamide;
N-[5-(2-{2-[4-(3'-aminomethyl-6-methoxybiphenyl-3-yloxy)phenyl]-ethylamino}-1-hydroxyethyl)-2-hydroxyphenyl]formamide;
N-[5-(2-{2-[4-(4'-aminomethyl-6-methoxybiphenyl-3-yloxy)phenyl]-ethylamino}-1-hydroxyethyl)-2-hydroxyphenyl]formamide;
4-(2-{2-[4-(3'-chloro-6-methoxybiphenyl-3-yloxy)phenyl]ethylamino}-1-hydroxyethyl)-2-hydroxymethylphenol;
5'-(4-{2-[2-hydroxy-2-(4-hydroxy-3-hydroxymethylphenyl)ethylamino]-ethyl}phenoxy)-2'-methoxybiphenyl-3-carbonitrile;
4-(2-{2-[4-(3'-aminomethyl-6-methoxybiphenyl-3-yloxy)phenyl]ethyl-amino}-1-hydroxyethyl)-2-hydroxymethylphenol; and
4-(2-{2-[4-(4'-aminomethyl-6-methoxybiphenyl-3-yloxy)phenyl]ethyl-amino}-1-hydroxyethyl)-2-hydroxymethylphenol.

As illustrated above, the compounds of the invention contain one or more chiral centers. Accordingly, the invention includes racemic mixtures, pure stereoisomers (i.e. individual enantiomers or diastereomers), and stereoisomer-enriched mixtures of such isomers, unless otherwise indicated. When a particular stereoisomer is shown, it will be understood by those skilled in the art, that minor amounts of other stereoisomers may be present in the compositions of this invention unless otherwise indicated, provided that the utility of the composition as a whole is not eliminated by the presence of such other isomers.

In particular, compounds of the invention contain a chiral center at the alkylene carbon in formulas (I) and (II) to which the hydroxy group is attached. When a mixture of stereoisomers is employed, it is advantageous for the amount of the stereoisomer with the (R) orientation at the chiral center bearing the hydroxy group to be greater than the amount of the corresponding (S) stereoisomer. When comparing stereoisomers of the same compound, the (R) stereoisomer is preferred over the (S) stereoisomer.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Representative alkyl groups include, by way of example, methyl, ethyl, n-propyl, isopropyl, n-butyl, sec-butyl, isobutyl, tert-butyl, n-pentyl, n-hexyl, and the like.

When a specific number of carbon atoms is intended for a particular term used herein, the number of carbon atoms is shown preceding the term. For example, the term "$C_{1-6}$alkyl" means an alkyl group having from 1 to 6 carbon atoms.

The term "alkoxy" means the monovalent group —O-alkyl, where alkyl is defined as above. Representative alkoxy groups include, by way of example, methoxy, ethoxy, propoxy, butoxy, and the like.

The term "alkenyl" means a monovalent unsaturated hydrocarbon group containing at least one carbon-carbon double bond, typically 1 or 2 carbon-carbon double bonds, and which may be linear or branched or combinations thereof. Representative alkenyl groups include, by way of example, vinyl, allyl, isopropenyl, but-2-enyl, n-pent-2-enyl, and n-hex-2-enyl, and the like.

The term "alkynyl" means a monovalent unsaturated hydrocarbon group containing at least one carbon-carbon triple bond, typically 1 carbon-carbon triple bond, and which may be linear or branched or combinations thereof. Representative alkynyl groups include, by way of example, ethynyl, propargyl, but-2-ynyl and the like.

The term "alkylenyl" means a divalent saturated hydrocarbon group which may be linear or branched or combinations thereof. Representative alkylenyl groups include, by way of example, methylene, ethylene, n-propylene, n-butylene, propane-1,2-diyl (1-methylethylene), 2-methylpropane-1,2-diyl (1,1-dimethylethylene) and the like.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "heteroaryl" means a monovalent aromatic group having a single ring or two fused rings and containing in the ring at least one heteroatom (typically 1 to 3 heteroatoms) selected from nitrogen, oxygen, and sulfur. Unless otherwise defined, such heteroaryl groups typically contain from 5 to 10 atoms total ring atoms. Representative heteroaryl groups include, by way of example, pyrroyl, isoxazolyl, isothiazolyl, pyrazolyl, pyridyl (or, equivalently, pyridinyl), oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, quinolyl, indolyl, isoquinolyl and the like, where the point of attachment is at any available carbon or nitrogen ring atom.

The term "heterocyclyl" or "heterocyclic ring" means a monovalent saturated or partially unsaturated cyclic non-aromatic group, which may be monocyclic or multicyclic (i.e., fused or bridged), and which contains at least one heteroatom (typically 1 to 3 heteroatoms) selected from nitrogen, oxygen, and sulfur. Unless otherwise defined, such heterocyclyl groups typically contain from 5 to 10 total ring atoms. Representative heterocyclyl groups include, by way of example, pyrrolidinyl, piperidinyl, piperazinyl, imidazolidinyl, morpholinyl, indoline-3-yl, 2-imidazolinyl, 1,2,3,4-tetrahydroisoquinolin-2-yl, quinuclidinyl, and the like.

The term "amino" means —NH$_2$.

The term "oxo" means (=O).

The term "halo" means a fluoro, chloro, bromo or iodo.

The term "compound" means a compound that was synthetically prepared or prepared in any other way, such as by metabolism.

The term "therapeutically effective amount" means an amount sufficient to effect treatment when administered to a patient in need of treatment.

The term "treatment" as used herein means the treatment of a disease or medical condition in a patient, such as a mammal (particularly a human) which includes:
 (a) preventing the disease or medical condition from occurring, i.e., prophylactic treatment of a patient;
 (b) ameliorating the disease or medical condition, i.e., eliminating or causing regression of the disease or medical condition in a patient;
 (c) suppressing the disease or medical condition, i.e., slowing or arresting the development of the disease or medical condition in a patient; or
 (d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, pulmonary diseases, such as asthma and chronic obstructive pulmonary disease (including chronic bronchitis and emphysema), as well as neurological disorders and cardiac disorders. $\beta_2$ Adrenergic receptor activity is also known to be associated with pre-term labor (see U.S. Pat. No. 5,872,126) and some types of inflammation (see International Patent Application Publication Number WO 99/30703 and U.S. Pat. No. 5,290,815).

The term "pharmaceutically-acceptable salt" means a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include, but are not limited to, acetic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Salts derived from fumaric, hydrobromic, hydrochloric, acetic, sulfuric, methanesulfonic, xinafoic, and tartaric acids are of particular interest.

Salts derived from pharmaceutically-acceptable inorganic bases include aluminum, ammonium, calcium, copper, ferric, ferrous, lithium, magnesium, manganic, manganous, potassium, sodium, zinc and the like. Ammonium, calcium, magnesium, potassium and sodium salts are of particular interest. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

The term "salt thereof" means a compound formed when the hydrogen of an acid is replaced by a cation, such as a metal cation or an organic cation and the like. Preferably, the salt is a pharmaceutically-acceptable salt, although this is not required for salts of intermediate compounds that are not intended for administration to a patient.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl(Fmoc); arylmethyl groups, such as benzyl(Bn), trityl(Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. For example, when $R^5$ or $R^6$ includes an amino or hydroxy group, additional protecting groups may be necessary to prevent these functional groups from undergoing undesired reactions. The choice of a suitable protecting group for a particular functional group, as well as suitable conditions for protection and deprotection, is well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

Removal of the protecting groups may be effected using conventional techniques. Typical procedures for the removal of amino-protecting groups and hydroxy-protecting groups include the following. Arylmethyl groups, such as a benzyl protecting group, are conveniently removed by catalytic hydrogenation in the presence of a Group VIII metal catalyst, such as palladium on carbon. A tert-butyldimethylsilyl group is conveniently removed by treatment with hydrogen fluoride, such as triethylamine trihydrofluoride.

The substituents and variables shown in the following synthetic processes or schemes have the definitions provided above unless otherwise indicated.

In one method of synthesis, compounds of formulas (I) and (II) are prepared as illustrated in Scheme A. (The substituents and variables shown in the following schemes have the definitions provided herein unless otherwise indicated.)

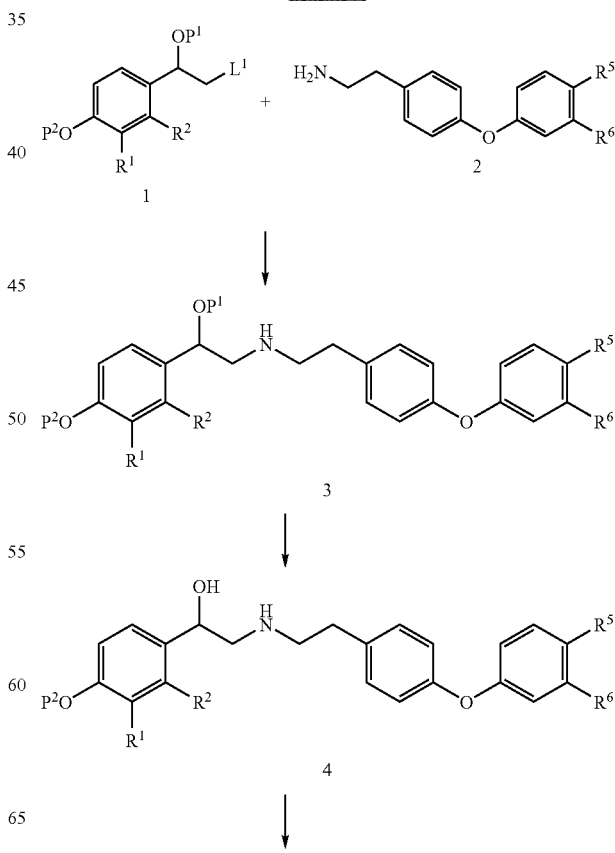

-continued

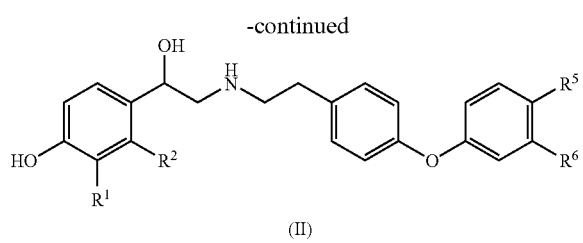

(II)

As shown in Scheme A, a compound of formula 1, (wherein $P^1$ and $P^2$ are hydroxy-protecting groups; and $L^1$ is a leaving group, such as bromide), is reacted with an amine compound of formula 2 to provide an intermediate compound of formula 3. Typically, this reaction is conducted in a polar aprotic solvent in the presence of a base. Suitable solvents include dimethylsulfoxide, dimethyl formamide, dimethylacetamide and the like. The reaction is typically heated at a temperature of between about 60° C. and about 140° C. for between about 0.25 and about 7 hours.

The protecting group $P^1$ is typically a silyl protecting group, which is typically removed from the intermediate of formula 3 using a fluoride reagent, for example triethylamine trihydrofluoride, or an acid, to provide an intermediate of formula 4.

The protecting group $P^2$ is typically a benzyl protecting group, which is typically removed from the intermediate of formula 4 using a Lewis acid, for example, boron trichloride, or by hydrogenation using a palladium on carbon catalyst.

Compounds of formula 1 are readily prepared by procedures known in the art, and are described, for example, in U.S. Pat. Nos. 6,653,323 B2 and 6,670,376 B1, which are incorporated herein by reference, and references therein.

Intermediates of formula 2 can be prepared from readily available starting materials, for example, by the procedure illustrated in Scheme B:

Scheme B

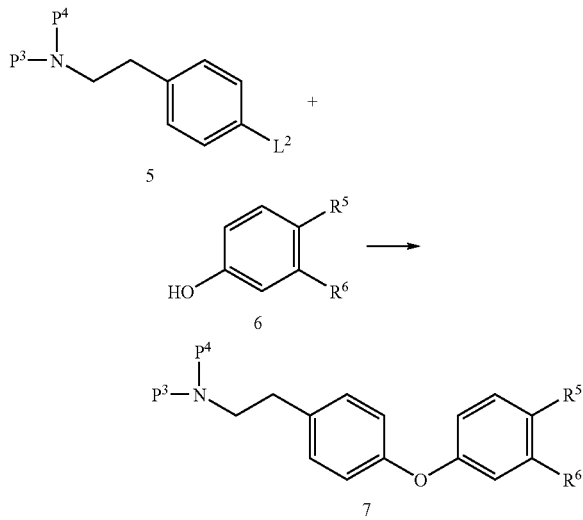

wherein one of $P^3$ and $P^4$ is an amino protecting group and the other of $P^3$ and $P^4$ is hydrogen, or $P^3$ and $P^4$ together with the N atom to which they are attached form an amino protecting group; and $L^2$ is a leaving group, such as halo. The protecting groups are removed from intermediate 7 to provide a compound of formula 2.

A protected amine 5 is coupled with a substituted phenol 6, typically in the presence of a base and a catalyst, such as cesium carbonate and copper (1) chloride, to provide an intermediate of formula 7. Then, the amino-protecting group is removed from the intermediate of formula 7 to provide a compound of formula 2. For example, when $P^3$ and $P^4$ together with the nitrogen atom to which they are attached form a phthalimido group, compound 7 can be reacted with hydrazine in dichloromethane at room temperature to remove the amino-protecting group to provide a compound of formula 2.

In another method, for example, when one of $R^5$ and $R^6$ is phenyl or heteroaryl, a compound of formula 3 can be synthesized as illustrated in Schemes C and D below:

Scheme C

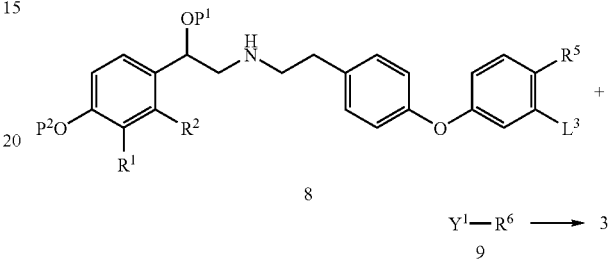

Scheme D

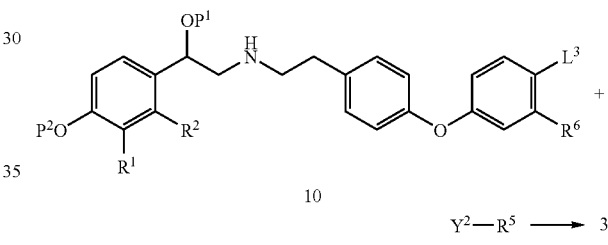

where $L^3$ is a leaving group, such as halo, and $Y^1$ and $Y^2$ are metal coupling agents. The compounds $Y^1$—$R^6$ or $Y^2$—$R^5$ are, for example, phenyl- or heteroaryl-boronic acid; phenyl- or heteroaryl-trialkyl-tin; phenyl or heteroaryl zinc halide; and phenyl or heteroaryl magnesium halide and the like. These reactions typically make use of a catalyst, such as a transition metal catalyst, such as soluble or insoluble complexes of platinum, palladium or nickel. For example, in Scheme C, when $Y^1$—$R^6$ is phenylboronic acid, $L^3$ can be halo, such as iodo, bromo, or chloro, and a palladium catalyst can be used. Reactions similar to Schemes C and D are described, for example, in U.S. Pat. No. 6,395,916, which is incorporated herein by reference.

A compound of formula 8 can be prepared by reacting a compound of formula 12:

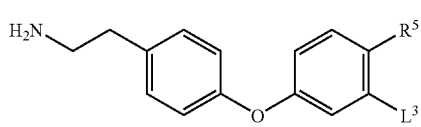

wherein $L^3$ is a leaving group, such as bromo, with a compound of formula 1. A compound of formula 10 can be made in a similar fashion.

A compound of formula 12 can be prepared by conventional procedures from, a compound of formula 5. For example, a compound of formula 12 in which $R^5$ is hydrogen and $L^3$ is chloro, can be prepared by reacting a compound of formula 5 with 3-chlorophenol, and then removing the amino-protecting group from the resulting product to provide a compound of formula 12.

Accordingly, the invention provides a process for preparing a compound of formula (I), the process comprising:

(a) reacting a compound of formula (i):

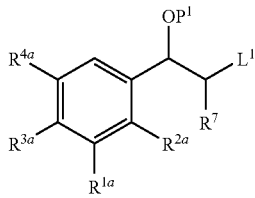
(i)

with a compound of formula (ii):

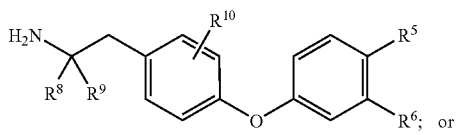
(ii)

(b) for a compound of formula (I) wherein $R^6$ is phenyl or heteroaryl, reacting a compound of formula (viii):

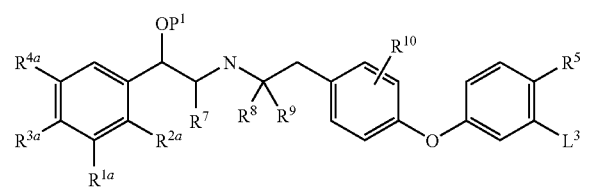
(viii)

with a compound of formula (ix):

$Y^1$—$R^6$ (ix)

in the presence of a transition metal catalyst; wherein:

$P^1$ is a hydroxy-protecting group;

each of $R^{1a}$, $R^{2a}$, $R^{3a}$, and $R^{4a}$ is defined to be the same as $R^1$, $R^2$, $R^3$, and $R^4$ in formula (I), or one or more of $R^{1a}$, $R^{2a}$, $R^{3a}$, and $R^{4a}$ is independently —$OP^2$, wherein $P^2$ is a hydroxy-protecting group;

$L^1$ is a leaving group;

$L^3$ is a leaving group;

$Y^1$—$R^6$ is selected from phenyl- or heteroaryl-boronic acid, phenyl- or heteroaryl-trialkyl-tin, phenyl or heteroaryl zinc halide, and phenyl or heteroaryl magnesium halide; and $R^5$, $R^6$, $R^7$, $R^8$, $R^9$, and $R^{10}$, are as defined for compounds of formula (I);

to provide a compound of formula (III):

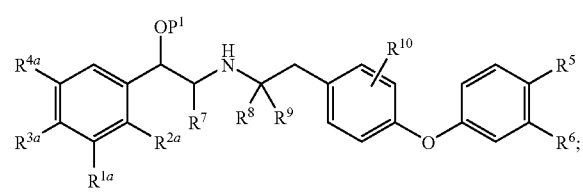
(III)

removing the protecting group $P^1$ to provide a compound of formula (IV):

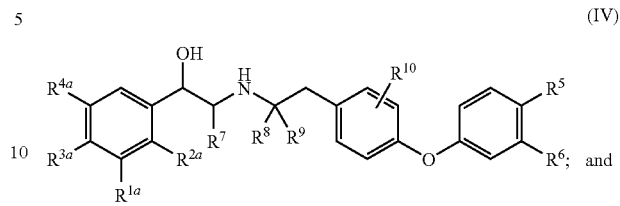
(IV)

when one or more of $R^{1a}$, $R^{2a}$, $R^{3a}$, and $R^{4a}$ are —$OP^2$, removing the protecting groups $P^2$; to provide a compound of formula (I), or a salt thereof.

Another method of preparing a compound of formula (III) is illustrated in Scheme E.

Scheme E

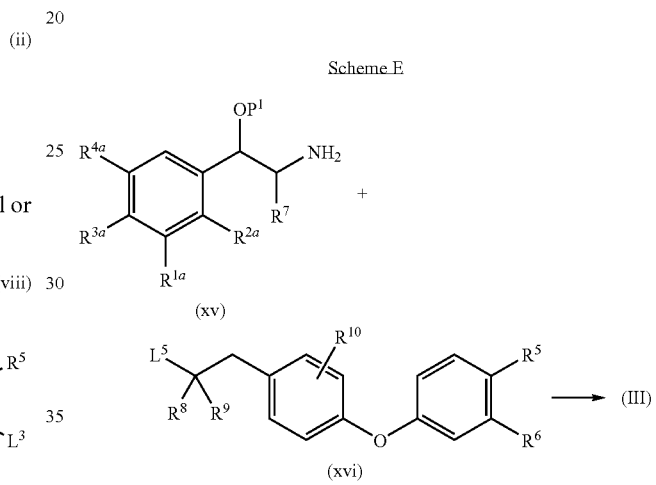

wherein $L^5$ is a leaving group.

Alternatively, a compound of formula (III) can be prepared, as illustrated in Scheme F, by reacting a compound of formula (xvii) with a compound of formula (xviii):

Scheme F

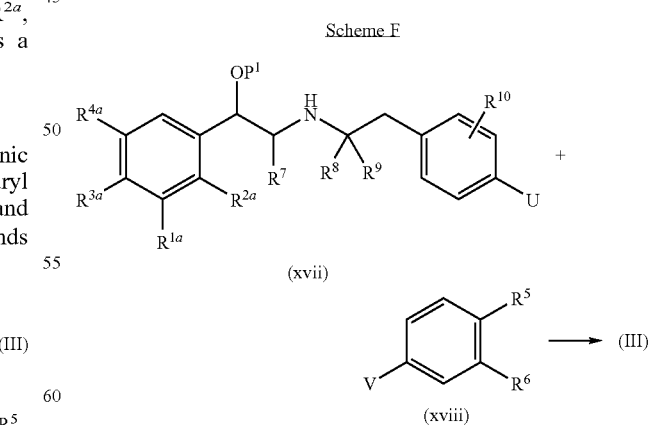

where one of U and V is a leaving group, such as chloro or fluoro, and the other of U and V is a hydroxy group. For Scheme F, the hydroxy group of the phenol becomes a phenoxy anion in the presence of a base.

Accordingly, the invention also provides a process for preparing a compound of formula (I), the process comprising:

(a) reacting a compound of formula (i) with a compound of formula (ii);

(b) for a compound of formula (I) wherein $R^6$ is phenyl or heteroaryl, reacting a compound of formula (viii) with a compound of formula (ix) in the presence of a transition metal catalyst;

(c) for a compound of formula (I) wherein $R^5$ is phenyl or heteroaryl, reacting a compound of formula (x):

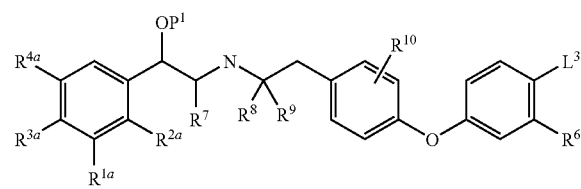

(x)

with a compound of formula (xi):

(xi)

in the presence of a transition metal catalyst, (d) reacting a compound of formula (xv):

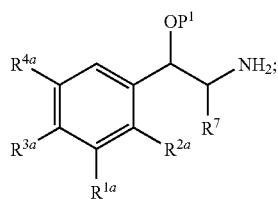

(xv)

with a compound of formula (xvi):

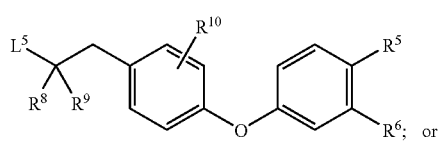

(xvi)

(e) reacting a compound of formula (xvii):

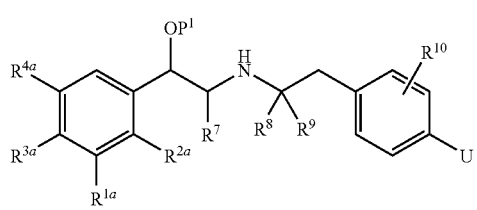

(xvii)

with a compound of formula (xviii):

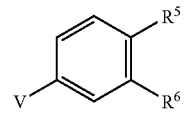

(xviii)

wherein:
$P^1$ is a hydroxy-protecting group;
each of $R^{1a}$, $R^{2a}$, $R^{3a}$, and $R^{4a}$ is defined to be the same as $R^1$, $R^2$, $R^3$, and $R^4$ in formula (I), or one or more of $R^{1a}$, $R^{2a}$, $R^{3a}$, and $R^{4a}$ is independently —$OP^2$, wherein $P^2$ is a hydroxy-protecting group;
$L^1$ is a leaving group;
$L^3$ is a leaving group;
$L^5$ is a leaving group;
one of U and V is a leaving group, and the other of U and V is a hydroxy group;
$Y^1$—$R^6$ and $Y^2$—$R^5$ are independently selected from phenyl- or heteroaryl-boronic acid, phenyl- or heteroaryl-trialkyl-tin, phenyl or heteroaryl zinc halide, and phenyl or heteroaryl magnesium halide; and
$R^5$, $R^6$, $R^7$, $R^8$, $R^9$, and $R^{10}$, are as defined for compounds of formula (I);
to provide a compound of formula (III); and
removing the protecting group $P^1$ and any $P^2$ protecting groups that are present, to provide a compound of formula (I), or a salt thereof.

The invention also provides a process for preparing a compound of formula (I), the process comprising deprotecting a compound of formula (III), by removing the protecting group $P^1$ and any $P^2$ protecting groups that are present, to provide a compound of formula (I), or a salt thereof.

A compound of formula (IV) can also be prepared by reacting an amine of formula (ii) with a compound of formula (xiii) or (xiv):

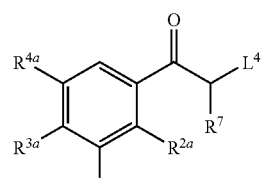

(xiii)

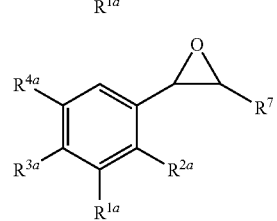

(xiv)

wherein $L^4$ is a leaving group, such as bromo.

The invention also provides a process for preparing a compound of formula (I), the process comprising deprotecting a compound of formula (IV), wherein at least one or more of $R^{1a}$, $R^{2a}$, $R^{3a}$, and $R^{4a}$ is —$OP^2$, by removing the protecting groups $P^2$, to provide a compound of formula (I), or a salt thereof.

Unless otherwise indicated in the processes described herein, protecting group $P^1$ and any $P^2$ groups that are present can be removed simultaneously or in any order.

In one embodiment of the invention, the processes described herein further comprise the step of forming a pharmaceutically-acceptable salt of the compound of formula (I).

In another embodiment of the invention, the processes described herein further comprise the following steps in any order:

(i) optionally separating a n enantiomer from a mixture of enantiomers; and (ii) optionally converting the product to a corresponding salt or solvate thereto;

In other embodiments, this invention is directed to the other processes described herein; and to the product prepared by any of the processes described herein.

The invention further provides a compound of formula (III), and a compound of formula (IV).

Further details regarding specific reaction conditions and other procedures for preparing representative compounds of the invention or intermediate thereto are described in the Examples below.

Pharmaceutical Compositions

The invention also provides pharmaceutical compositions comprising a compound of the invention. Accordingly, the compound, preferably in the form of a pharmaceutically-acceptable salt, can be formulated for any suitable form of administration, such as oral or parenteral administration, or administration by inhalation.

By way of illustration, the compound can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common carriers and excipients, such as cornstarch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarmellose, microcrystalline cellulose, cornstarch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a solubilizing agent, for example, a cyclodextrin; and an antioxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or Transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Conventional nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 µm.

A typical formulation for use in a conventional nebulizer device is an isotonic aqueous solution of a pharmaceutical salt of the active agent at a concentration of the active agent of between about 0.05 µg/mL and about 1 mg/mL. Suitable nebulizer devices are provided commercially, for example, by PARI GmbH (Starnberg, Germany). Other nebulizer devices have been disclosed, for example, in U.S. Pat. No. 6,123,068.

DPI's typically administer a therapeutic agent in the form of a free flowing powder that can be dispersed in a patient's air-stream during inspiration. Alternative DPI devices which use an external energy source to disperse the powder are also being developed. In order to achieve a free flowing powder, the therapeutic agent can be formulated with a suitable excipient (e.g., lactose or starch). A dry powder formulation can be made, for example, by combining dry lactose particles with micronized particles of a suitable form, typically a pharmaceutically-acceptable salt, of a compound of the invention (i.e. the active agent) and dry blending. Alternatively, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalkanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.001% to about 2% by weight of a compound of the invention, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing a compound of the invention, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,227.

In an alternative preparation, a suspension formulation is prepared by spray drying a coating of surfactant on micronized particles of a pharmaceutical salt of active compound. (See, for example, WO 99/53901 and WO 00/61108.) For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

It will be understood that any form of the compounds of the invention, (i.e. free base, pharmaceutical salt, or solvate) that is suitable for the particular mode of administration, can be used in the pharmaceutical compositions discussed above.

The active compounds are useful as a $\beta_2$ adrenergic receptor agonist and therefore are useful for treating medical diseases or conditions mediated by $\beta_2$ adrenergic receptors or associated with $\beta_2$ adrenergic receptor activity in a mammal, i.e. medical conditions which are ameliorated by treatment with a $\beta_2$ adrenergic receptor agonist. Such medical conditions include but are not limited to a pulmonary disease, such as asthma or chronic obstructive pulmonary disease, pre-term labor, a neurological disorder, a cardiac disorder, or inflammation.

The active compounds are effective over a wide dosage range and are generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agents for inhalation administration are in the general range of from about 0.05 µg/day to about 1000 µg/day, including from about 0.11 µg/day to about 500 µg/day. It will be understood that the fraction of active agent delivered to the lung characteristic of particular delivery devices is taken into account in determining suitable doses for inhalation administration.

A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 µg/day to about 100 mg/day, such as from about 0.5 to about 1000 µg/day.

Among other properties, compounds of the invention are potent and selective agonists of the $\beta_2$ adrenergic receptor. In particular, compounds of the invention are selective for the $\beta_2$ adrenergic receptor as compared with the $\beta_1$ and $\beta_3$ adrenergic receptors.

The invention thus provides a method of treating a mammal having a disease or condition associated with $\beta_2$ adrenergic receptor activity, the method comprising administering to the mammal a therapeutically effective amount of a compound of the invention or of a pharmaceutical composition comprising a compound of the invention.

The present active agents can also be co-administered with one or more other therapeutic agents. For example, the present agents can be administered in combination with one or more therapeutic agents selected from anti-inflammatory agents (e.g. corticosteroids and non-steroidal anti-inflammatory agents (NSAIDs), anticholinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising a compound of the invention together with one or more other therapeutic agents, for example, an anti-inflammatory agent, an anticholinergic agent, another $\beta_2$ adrenergic receptor agonist, an antiinfective agent or an antihistamine, such as a corticosteroid, an anticholinergic agent, or a PDE4 inhibitor.

The other therapeutic agents can be used in the form of pharmaceutically-acceptable salts or solvates. As appropriate, the other therapeutic agents can be used as optically pure stereoisomers.

Further, the invention also provides a pharmaceutical composition comprising a therapeutically effective amount of a compound of the invention, a pharmaceutically-acceptable carrier, and a therapeutically effective amount of one or more other therapeutic agents, i.e., where the other therapeutic agent is selected from anti-inflammatory agents (e.g., corticosteroids and non-steroidal anti-inflammatory agents (NSAIDs)), anticholinergic agents (particularly muscarinic receptor antagonists), other $\beta_2$ adrenergic receptor agonists, antiinfective agents (e.g., antibiotics or antiviral), antihistamines, and a phosphodiesterase 4 (PDE4) inhibitor; such as an anti-inflammatory agent, an anticholinergic agent, another $\beta_2$ adrenergic receptor agonist, an antiinfective agent, or an antihistamine.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester, $6\alpha,9\alpha$-difluoro-$11\beta$-hydroxy-$16\alpha$-methyl-3-oxo-$17\alpha$-propionyloxy-androsta-1,4-diene-$17\beta$-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, PPR-106541, and ST-126. Preferred corticosteroids include fluticasone propionate, $6\alpha,9\alpha$-difluoro-$11\beta$-hydroxy-$16\alpha$-methyl-$17\alpha$-[(4-methyl-1,3-thiazole-5-carbonyl)oxy]-3-oxo-androsta-1,4-diene-$17\beta$-carbothioic acid S-fluoromethyl ester and $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester, more preferably $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester.

Suitable NSAIDs include sodium cromoglicate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody ($\alpha$IL antibody), specifically, an $\alpha$IL-4 therapy, an $\alpha$IL-13 therapy, or a combination thereof); or inhibitors of cytokine synthesis. Suitable other $\beta_2$-adrenoreceptor agonists include salmetrol (e.g. as the xinofoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. Representative phosphodiesterase-4 (PDE4) inhibitors or mixed PDE3/PDE4 inhibitors include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically-acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-354), and hexocyclium methylsulfate (Tral, CAS-115-63-9). See also cyclopentolate hydrochloride (CAS-5870-29-1), tropicamide (CAS-1508-75-4), trihexylhenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperazine and phenothiazines. Second generation antagonists, which are non-sedating, have a similar structure-activity relationship in that they retain the core ethylene group (the alkylamines) or mimic a tertiary amine group with piperazine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically-acceptable salt.

Azelastine hydrochloride is yet another $H_1$ receptor antagonist which may be used in combination with a compound of the invention.

Examples of preferred anti-histamines include methapyrilene and loratadine.

The invention thus provides, in a further aspect, a combination comprising a compound of formula (I) or a pharmaceutically-acceptable salt or solvate or stereoisomer thereof and a corticosteroid. In particular, the invention provides a combination wherein the corticosteroid is fluticasone propionate or wherein the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester or 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising a compound of formula (I) or a pharmaceutically-acceptable salt or solvate or stereoisomer thereof and a PDE4 inhibitor.

The invention thus provides, in a further aspect, a combination comprising a compound of formula (I) or a pharmaceutically-acceptable salt or solvate or stereoisomer thereof and an anticholinergic agent.

The invention thus provides, in a further aspect, a combination comprising a compound of formula (I) or a pharmaceutically-acceptable salt or solvate or stereoisomer thereof and an antihistamine.

The invention thus provides, in a further aspect, a combination comprising a compound of formula (I) or a pharmaceutically-acceptable salt or solvate or stereoisomer thereof together with a PDE4 inhibitor and a corticosteroid.

The invention thus provides, in a further aspect, a combination comprising a compound of formula (I) or a pharmaceutically-acceptable salt or solvate or stereoisomer thereof together with an anticholinergic agent and a corticosteroid.

As used in the embodiments described herein, the term, "a compound of formula (I)" includes a compound of formula (II) and preferred groups thereof, and any individually disclosed compound or compounds.

Accordingly, the pharmaceutical compositions of the invention can optionally comprise combinations of a compound of formula (I) or a pharmaceutically-acceptable salt or solvate or stereoisomer thereof with one or more other therapeutic agents, as described above.

The individual compounds of such combinations may be administered either sequentially or simultaneously in separate or combined pharmaceutical compositions. Appropriate doses of known therapeutic agents will be readily appreciated by those skilled in the art. Methods of treatment of the invention, therefore, include administration of the individual compounds of such combinations either sequentially or simultaneously in separate or combined pharmaceutical compositions.

Thus, according to a further aspect, the invention provides a method of treating a mammal having a disease or condition associated with $\beta_2$ adrenergic receptor activity, the method comprising administering to the mammal a therapeutically effective amount of a combination of a compound of formula (I) or a pharmaceutically-acceptable salt or solvate or stereoisomer thereof with one or more other therapeutic agents.

Since compounds of the invention are $\beta_2$ adrenergic receptor agonists, such compounds are also useful as research tools for investigating or studying biological systems or samples having $\beta_2$ adrenergic receptors, or for discovering new $\beta_2$ adrenergic receptor agonists. Moreover, since compounds of the invention exhibit selectivity for $\beta_2$ adrenergic receptors as compared with binding and functional activity at receptors of other $\beta$ adrenergic subtypes, such compounds are also useful for studying the effects of selective agonism of $\beta_2$ adrenergic receptors in a biological system or sample. Any suitable biological system or sample having $\beta_2$ adrenergic receptors may be employed in such studies which may be conducted either in vitro or in vivo.

Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of agonizing the $\beta_2$ adrenergic receptor are determined using conventional procedures and equipment, such as radioligand binding assays and functional assays, for example the assay for ligand-mediated changes in intracellular cyclic adenosine monophosphate (cAMP) described below, or assays of a similar nature. A $\beta_2$ adrenergic receptor-agonizing amount of a compound of the invention will typically range from about 1 nanomolar to about 1000 nanomolar. When compounds of the invention are used as research tools for discovering new $\beta_2$ adrenergic receptor agonists, the invention also includes, as separate embodiments, both the generation of comparison data (using the appropriate assays) and the analysis of the test data to identify test compounds of interest.

Accordingly, the invention provides a method of studying a biological system or sample comprising a $\beta_2$ adrenergic receptor, the method comprising: (a) contacting the biological system or sample with a compound of formula (I); and (b) determining the effects caused by the compound on the biological system or sample.

The following non-limiting examples illustrate representative pharmaceutical compositions of the invention. Additional suitable carriers for formulations of the active compounds of the present invention can also be found in *Remington: The Science and Practice of Pharmacy*, 20th Edition, Lippincott Williams & Wilkins, Philadelphia, Pa., 2000.

FORMULATION EXAMPLE A

This example illustrates the preparation of a representative pharmaceutical composition for oral administration of a compound of this invention:

| Ingredients | Quantity per tablet, (mg) |
| --- | --- |
| Active Ingredient | 1 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
| --- | --- |
| Active Ingredient | 1 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
| --- | --- |
| Active Compound | 3 mg |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.1 mg |
| Sodium Acetate Buffer Solution (0.4M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

FORMULATION EXAMPLE F

This example illustrates the preparation of a representative pharmaceutical composition for topical application of a compound of this invention.

| Ingredients | grams |
| --- | --- |
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE G

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

FORMULATION EXAMPLE H

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
| --- | --- |
| Pharmaceutical salt of active compound | 0.2 |
| Lactose | 25 |

The pharmaceutical salt of active compound is micronized prior to blending with lactose. The contents of the cartridges are administered using a powder inhaler.

FORMULATION EXAMPLE I

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 μg and about 100 μg of active drug ingredient per dose.

FORMULATION EXAMPLE J

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 sum in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

FORMULATION EXAMPLE K

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into canisters with pressurized 1,1,1,2,3,3,3-heptafluoro-n-propane.

The following examples are offered to illustrate the invention, and are not to be construed in any way as limiting the scope of the invention.

| Abbreviations | |
|---|---|
| % Eff | % efficacy |
| ATCC | American Type Culture Collection |
| BSA | Bovine Serum Albumin |
| cAMP | Adenosine 3':5'-cyclic monophosphate |
| DMEM | Dulbecco's Modified Eagle's Medium |
| DMSO | Dimethyl sulfoxide |
| EDTA | Ethylenediaminetetraacetic acid |
| Emax | maximal efficacy |
| FBS | Fetal bovine serum |
| Gly | Glycine |
| HEK-293 | Human embryonic kidney - 293 |
| PBS | Phosphate buffered saline |
| rpm | rotations per minute |
| Tris | Tris(hydroxymethyl)aminomethane |

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using Tests A-C below, or can be demonstrated using other tests that are known in the art.

Membrane Preparation from Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 μg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @ 4° C., one tablet of "Complete Protease Inhibitor Cocktail Tablets with 2 mM EDTA" per 50 mL buffer (Roche cat.# 1697498, Roche Molecular Biochemicals, Indianapolis, Ind.)) and homogenized using a tight-fitting Dounce glass homogenizer (20 strokes) on ice. The homogenate was centrifuged at 20,000×g, the pellet was washed once with lysis buffer by resuspension and centrifugation as above. The final pellet was resuspended in membrane buffer (75 mM Tris/HCl pH 7.4, 12.5 mM $MgCl_2$, 1 mM EDTA @ 25° C.). Protein concentration of the membrane suspension was determined by the method of Bradford (Bradford M M., *Analytical Biochemistry*, 1976, 72, 248-54). Membranes were stored frozen in aliquots at −80° C.

Test A

Radioligand Binding Assay on Human $\beta_1$ and $\beta_2$ Adrenergic Receptors Binding assays were performed in 96-well microtiter plates in a total assay volume of 100 μL with 5 μg membrane protein for membranes containing the human $\beta_2$ adrenergic receptor, or 2.5 μg membrane protein for membranes containing the human β1 adrenergic receptor in assay buffer (75 mM Tris/HCl pH 7.4 @ 25° C., 12.5 mM $MgCl_2$, 1 mM EDTA, 0.2% BSA). Saturation binding studies for determination of $K_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM-200 nM. Displacement assays for determination of $pK_i$ values of compounds were done with [$^3$H]dihydroalprenolol at 1 nM and 10 different concentrations of compound ranging from 40 pM-10 μM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 μM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @4° C., 12.5 mM $MgCl_2$, 1 mM EDTA) to remove unbound radioactivity. Plates were dried, 50 μL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM alprenolol. $K_i$ values for compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099-108). The receptor subtype selectivity was calculated as the ratio of $K_i(\beta_1)/K_i(\beta_2)$. Compounds of the invention demonstrated greater binding at the $\beta_2$ adrenergic receptor than at the $\beta_1$ adrenergic receptor, i.e. $K_i(\beta_1) > K_i(\beta_2)$ with selectivity greater than about 10. In particular, the compound of Example 1 demonstrated greater binding at the $\beta_2$ adrenergic receptor than at the $\beta_1$ adrenergic receptor, i.e. $K_i(\beta_1) > K_i(\beta_2)$ with selectivity of about 18.

Test B

Whole-Cell cAMP Flashplate Assays with Cell Lines Heterologously Expressing Human $\beta_1$ Adrenoceptor, $\beta_2$ Adrenoceptor, and $\beta_3$ Adrenoceptor, Respectively A HEK-293 cell line stably expressing cloned human $\beta_1$ adrenergic receptor (clone H34.1) was grown to about 70%-90% confluency in medium consisting of DMEM supplemented with 10% FBS and 500 µg/mL Geneticin. A HEK-293 cell line stably expressing cloned human $\beta_2$-adrenoceptor (clone H24.14) was grown in the same medium to full confluency. A CHO-K1 cell line stably expressing cloned human $\beta_3$-adrenoceptor was grown to about 70%-90% confluency in Ham's F-12 medium supplemented with 10% FBS and with 800 µg/mL Geneticin added to every fifth passage. The day before the assay, cultures were switched to the same growth-media without antibiotics.

cAMP assays were performed in a radioimmunoassay format using the Flashplate Adenylyl Cyclase Activation Assay System with $^{125}$I-cAMP (NEN SMPOO4, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. For cells expressing the $\beta_1$-adrenoceptor, 10 nM ICI 118,551 were added to the stimulation buffer, and cells were incubated for 10 min at 37° C. Cells were used at final concentrations of 30,000, 40,000 and 70,000 cells/well for the $\beta_1$-adrenoceptor-, the $\beta_2$-adrenoceptor- and the $\beta_3$-adrenoceptor expressing cells, respectively. Compounds were dissolved to a concentration of 10 mM in DMSO, then diluted to 1 mM in 50 mM Gly-HCl pH 3.0, and from there serially diluted into assay buffer (75 mM Tris/HCl pH 7.4 @ 25° C., 12.5 mM MgCl$_2$, 1 mM EDTA, 0.2% BSA). Compounds were tested in the assay at 11 different concentrations, ranging from 10 µM to 9.5 µM. Reactions were incubated for 10 min at 37° C. and stopped by addition of 100 µL ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 3-parameter model for sigmoidal dose-response (Hill slope=1). Agonist potencies were expressed as pEC$_{50}$ values. Functional $\beta_2/\beta_1$ selectivity was defined as the ratio pEC$_{50}(\beta_1)$/EC$_{50}(\beta_2)$, and correspondingly functional $\beta_2/\beta_3$ selectivity was defined as the ratio pEC$_{50}(\beta_3)$/EC$_{50}(\beta_2)$.

Compounds of the invention demonstrated potent activity at the $\beta_2$ adrenergic receptor in this assay, as evidenced by pEC$_{50}$ values greater than about 7. In addition, the compounds tested demonstrated selectivity in functional activity at the $\beta_2$ receptor as compared with functional activity at the $\beta_1$ and $\beta_3$ receptors. In particular, compounds of the invention that were tested in this assay demonstrated pEC$_{50}(\beta_2)$/pEC$_{50}(\beta_1)$ ratios of greater than about 40 and pEC$_{50}(\beta_2)$/pEC$_{50}(\beta_3)$ ratios of greater than about 30.

Test C

Whole-Cell Camp Flashplate Assay with a Lung Epithelial Cell Line Endogenously Expressing Human $\beta_2$ Adrenergic Receptor For the determination of agonist potencies and efficacies (intrinsic activities) in a cell line expressing endogenous levels of $\beta_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat #181-500, Biosource International, Camarillo, Calif.). The day before the assay, medium was switched to LHC-8 (No epinephrine or retinoic acid, cat #141-500, Biosource International, Camarillo, Calif.).

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and resuspended in stimulation buffer prewarmed to 37° C. at a final concentration of 600,000 cells/mL. Cells were used at a final concentration of 30,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM MgCl$_2$, 1 mM EDTA, 0.2% BSA).

Compounds were tested in the assay at 10 different concentrations, ranging from 10 µM to 40 µM. Maximal response was determined in the presence of 10 µM Isoproterenol. Reactions were incubated for 10 min at 37° C. and stopped by addition of 100 µl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response with variable slope. Compound efficacy (% Eff) was calculated from the ratio of the observed Emax (TOP of the fitted curve) and the maximal response obtained for 10 µM isoproterenol and was expressed as % Eff relative to isoproterenol. Compounds of the invention that were tested in this assay demonstrated a % Eff greater than about 50.

EXAMPLES

General: Unless noted otherwise, reagents, starting material and solvents were purchased from commercial suppliers, for example Sigma-Aldrich (St. Louis, Mo.), J. T. Baker (Phillipsburg, N.J.), and Honeywell Burdick and Jackson (Muskegon, Md.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent (CD$_3$OD, CDCl$_3$, or DMSO-d$_6$), and spectra were acquired with a Varian Gemini 2000 instrument (300 MHz) under standard parameters; and mass spectrometric identification was performed by an electrospray ionization method (ESMS) with a Perkin Elmer instrument (PE SCFEX API 150 EX).

Example 1

Synthesis of 8-Hydroxy-5-((R)-1-hydroxy-2-{2-[4-(6-methoxybiphenyl-3-yloxy)phenyl]ethylamino}ethyl)-1H-quinolin-2-one

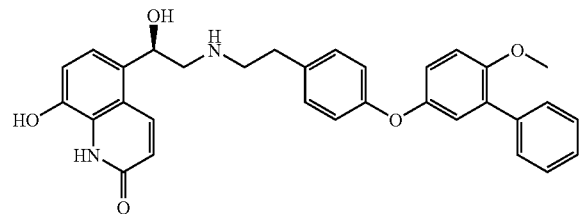

Step (a). Preparation of 6-Methoxybiphenyl-3-ol

A solution of 6-methoxybiphenyl-3-ylamine (3.4 g) in acetic acid (6 mL) was added to a mixture of concentrated sulfuric acid (1.4 mL) and ice (30 g). The slurry was cooled to 0° C. and a solution of sodium nitrite (1.24 g) in water (9 mL) was added slowly, maintaining the temperature below 5° C. The mixture was stirred at 0° C. for 0.5 h, then added via syringe under the surface of refluxing 2M sulfuric acid (150 mL). The reaction mixture was refluxed for 1 h, then allowed to cool to room temperature. The solution was extracted with dichloromethane (2×200 mL). The combined organics were dried over sodium sulfate and concentrated in vacuo. The residue was purified by flash column chromatography (SiO$_2$, dichloromethane) to afford the title intermediate (2.1 g) as a dark oil. m/z: [M$^+$] calcd for C$_{13}$H$_{12}$O$_2$ 200.1; found 200.1. $^1$H NMR (300 MHz, DMSO-d$_6$): 8.92 (s, 1H), 7.32-7.16 (m, 5H), 6.78 (d, 1H, J=8.5 Hz), 6.57 (m, 2H), 3.51 (s, 1H).

Step (b). Preparation of 2-[2-(4-Iodophenyl)ethyl]-1H-isoindole-1,3(2H)-dione

A solution of 2-(4-iodophenyl)ethylamine (7.08 g) and phthalic anhydride (4.24 g) in acetic acid (100 mL) was refluxed for 4 h. The solvent was evaporated and the residue triturated with ethanol (100 mL). The solid was filtered to afford the title intermediate (7.0 g) as a white solid.

Step (c). Preparation of 2-{2-[4-(6-Methoxybiphenyl-3-yloxy)phenyl]ethyl}isoindole-1,3-dione A slurry of the product of step (a) (400 mg) and cesium carbonate (652 mg) in N-methylpyrrolidinone (2 mL) was degassed by bubbling nitrogen gas through it for 10 minutes. To this slurry was then added copper (I) chloride (50 mg), 2,2,6,6-tetramethylheptane-3,5-dione (45 mg), and the product of step (b) (377 mg). The reaction mixture was warmed to 120° C. and stirred for 4 h before being allowed to cool to room temperature. The solution was diluted with methyl-tert-butyl ether (20 mL), washed with 1M hydrochloric acid (20 mL) then 1M sodium hydroxide (20 mL), then dried over sodium sulfate and concentrated in vacuo. The residue was purified by flash column chromatography (SiO$_2$, 250:1:0.5 dichloromethane:methanol:acetic acid) to afford the title intermediate (170 mg) as a clear oil.

Step (d). Preparation of 2-[4-(6-Methoxybiphenyl-3-yloxy)phenyl]ethylamine

A solution of the product of step (c) (170 mg) and hydrazine (2 mL) in dichloromethane (10 mL) was stirred at room temperature for 3 h then diluted with water (20 mL) and dichloromethane (50 mL). The organics were separated, washed with water (2×20 mL), dried over sodium sulfate and evaporated to afford the title intermediate (110 mg). m/z: [M+H$^+$] calcd for C$_{21}$H$_{21}$NO$_2$ 320.2; found 320.3.

Step (e). Preparation of 8-Benzyloxy-5-((R)-1-(tert-butyldimethylsilanyloxy)-2-{2-[4-(6-methoxybiphenyl-3-yloxy)phenyl]ethylamino}ethyl)-1H-quinolin-2-one A slurry of the product of step (d) (919 mg), 8-(benzyloxy)-5-[(R)-2-bromo-1-(tert-butyldimethylsilanyloxy)ethyl]-1H-quinolin-2-one (909 mg), potassium carbonate (771 mg) and sodium iodide (418 mg) in DMSO was heated at 90° C. for 5 h. The mixture was allowed to cool then diluted with water (10 mL). The solution was extracted with dichloromethane (2×30 mL). The combined organics were dried over sodium sulfate and the solvent removed in vacuo. The residue was purified by column chromatography (40:2:1 dichloromethane:methanol:acetic acid) to afford the title intermediate (1.0 g) as a clear oil. m/z: [M+H$^+$] calcd for C$_{45}$H$_{50}$N$_2$O$_5$Si 727.4; found 727.8.

Step (f). Preparation of 8-Benzyloxy-5-((R)-1-hydroxy-2-{2-[4-(6-methoxy-biphenyl-3-yloxy)phenyl]ethylamino}ethyl)-1H-quinolin-2-one A solution of the product of step (e) (500 mg) and triethylamine trihydrofluoride (0.34 mL) in tetrahydrofuran (5 mL) was stirred at room temperature for 16 h. The solution was diluted with isopropyl acetate (20 mL) and sodium hydroxide (1M, 20 mL). The organics were separated, dried over sodium sulfate and evaporated to afford the title intermediate (200 mg) as a clear oil. m/z: [M+H$^+$] calcd for C$_{39}$H$_{36}$N$_2$O$_5$ 613.3; found 613.5

Step (g). Synthesis of 8-Hydroxy-5-((R)-1-hydroxy-2-{2-[4-(6-methoxy-biphenyl-3-yloxy)phenyl]ethylamino}ethyl)-1H-quinolin-2-one A slurry of the product of step (g) (200 mg) and palladium hydroxide (20% w/w on carbon, 50 mg) in a solution of 1:1 dichloromethane:methanol (10 mL) was stirred under an atmosphere of hydrogen for 3 h. The catalyst was filtered off, the filtrate evaporated and the residue purified by reverse phase HPLC to afford the title compound (110 mg) in the form of a white solid as a trifluoroacetate salt. m/z: [M+H$^+$] calcd for C$_{32}$H$_{30}$N$_2$O$_5$ 523.2; found 523.6. $^1$H NMR (300 MHz, DMSO-d$_6$): 10.38 (d, 1H, J=19.3 Hz), 8.57 (br s, 1H), 8.00 (d, 1H, J=9.9 Hz), 7.35-7.16 (m, 6H), 7.11 (d, 2H, J=8.8 Hz), 7.04-6.99 (m, 2H), 6.89-6.81 (m, 4H), 6.46 (d, 1H, J=8.3 Hz), 6.06 (br s, 1H), 5.18 (d, 1H, J=9.1 Hz), 3.63 (s, 3H), 3.07-2.78 (m, 7H).

Example 2

Synthesis of 5-((R)-2-{2-[4-(Biphenyl-3-yloxy)phenyl]ethylamino}-1-hydroxyethyl)-8-hydroxy-1H-quinolin-2-one

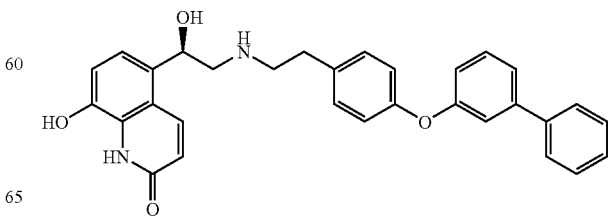

Step (a). Preparation of 2-{2-[4-(3-Chlorophenoxy)phenyl]ethyl}isoindole-1,3-dione A slurry of 3-chlorophenol (2.4 mL) and cesium carbonate (6.1 g) in N-methylpyrrolidinone (15 mL) was degassed by bubbling nitrogen gas through it for 10 minutes. Copper (I) chloride (462 mg), 2,2,6,6-tetramethylheptane-3,5-dione (425 mg), and the product of Example 1, step (b), 2-[2-(4-iodophenyl)ethyl]-1H-isoindole-1,3(2H)-dione (3.5 g) were then added to the slurry, which was then warmed to 120° C. and stirred for 3 h before being allowed to cool to room temperature. The solution was diluted with dichloromethane (100 mL), washed with 1M hydrochloric acid (2×50 mL) then brine (2×50 mL), dried over sodium sulfate and concentrated in vacuo. The residue was purified by reverse phase HPLC to afford the title intermediate (900 mg) as a clear oil. m/z: [M+H$^+$] calcd for $C_{22}H_{16}ClNO_3$ 378.09; found 378.3.

Step (b). Preparation of 2-[4-(3-Chlorophenoxy)phenyl]ethylamine

A solution of the product of step (a) (900 mg) and hydrazine (4 mL) in dichloromethane (10 mL) was stirred at room temperature for 4 h. The mixture was diluted with water (20 mL) and dichloromethane (80 mL). The organic layer was separated, washed with water (2×20 mL) and brine (20 ml), dried over sodium sulfate and evaporated to leave an oil/solid residue. The residue was taken up in methanol (20 mL) and filtered to remove solid material. The filtrate was evaporated to afford the title intermediate (470 mg) as a clear oil.

Step (c). Preparation of 8-Benzyloxy-5-((R)-1-(tert-butyldimethylsilanyloxy)-2-{2-[4-(3-chlorophenoxy)phenyl]ethylamino}ethyl)-1H-quinolin-2-one A slurry of the product of step (b) (1.39 g), 8-(benzyloxy)-5-[(R)-2-bromo-1-(tert-butyldimethylsilanyloxy)ethyl]-1H-quinolin-2-one (2.49 g), sodium iodide (1.14 g) and potassium carbonate (2.11 g) in DMSO (7 mL) was heated at 90° C. for 5 h. The solution was allowed to cool, diluted with dichloromethane (60 mL) and washed with water (4×30 mL) then brine (40 mL). The organics were dried over sodium sulfate, concentrated in vacuo and the residue purified by reverse phase HPLC to afford the title intermediate (1.85 g) as a clear oil. m/z: [M+H$^+$] calcd for $C_{38}H_{43}ClN_2O_4Si$ 655.3; found 655.5.

Step (d). Preparation of 8-Benzyloxy-5-[(R)-2-{2-[4-(biphenyl-3-yloxy)phenyl]ethyl-amino}-1-(tert-butyldimethylsilanyloxy)ethyl]-1H-quinolin-2-one A slurry of the product of step (c) (200 mg), phenylboronic acid (84 mg), sodium tert-butoxide (154 mg) and [(tert-butyl)$_2$ P(OH)]$_2$PdCl$_2$ (22 mg) in toluene (2 mL) was refluxed for 16 h. The mixture was allowed to cool, diluted with dichloromethane (10 mL) and washed with water (2×10 mL) then brine (10 mL). The organics were dried over sodium sulfate, concentrated in vacuo to yield the title intermediate (275 mg) which was used directly in the next step without further purification. m/z: [M+H$^+$] calcd for $C_{44}H_{48}N_2O_4Si$ 697.4; found 697.5.

Step (e). Preparation of 8-Benzyloxy-5-[(R)-2-{2-[4-(biphenyl-3-yloxy)phenyl]ethyl-amino}-1-hydroxyethyl]-1H-quinolin-2-one The product of step (d) (275 mg) and triethylamine trihydrofluoride (1.0 mL) in tetrahydrofuran (10 mL) was stirred at room temperature for 16 h. The solution was diluted with sodium hydroxide (0.5M, 10 mL), extracted with dichloromethane (2×10 mL) and the combined organics dried over sodium sulfate and evaporated to afford the title intermediate (105 mg), which was used directly in the next step without further purification.

Step (f). Synthesis of 8-Hydroxy-5-[(R)-2-{2-[4-(biphenyl-3-yloxy)phenyl]ethyl-amino}-1-hydroxyethyl]-1H-quinolin-2-one A slurry of the product of step (e) (105 mg) and palladium hydroxide (100 mg) in a solution of 1:1 acetic acid:tetrahydrofuran (10 mL) was stirred under an atmosphere of hydrogen for 24 h. The catalyst was filtered off, the filtrate evaporated and the residue purified by reverse phase HPLC to afford the title compound (16 mg) in the form of a white solid as a trifluoroacetate salt. m/z: [M+H$^+$] calcd for $C_{31}H_{28}N_2O_4$, 493.2; found 493.5. $^1$H NMR (300 MHz, DMSO-d$_6$): 10.40 (d, 1H, J=20 Hz), 8.60 (br s, 1H), 8.01 (d, 1H, J=8.8 Hz), 7.49 (d, 2H, J=8.2 Hz), 7.14-7.34 (m, 7H), 7.03 (d, 1H, J=7.4 Hz), 6.93 (d, 2H, J=7.4 Hz), 6.86-6.82 (m, 2H), 6.46 (d, 1H, J=9.9 Hz), 6.07 (s, 1H), 5.18 (m, 1H), 3.19-2.82 (m, 6H).

Using procedures similar to those described in the Examples and General Synthetic Procedures section herein, and starting with the appropriate reagents, the following compounds listed in Table A can be prepared:

TABLE A

| Ex. | R$^1$ | R$^2$ | R$^5$ | R$^6$ |
|---|---|---|---|---|
| 3 | —NHC(=O)CH=CH— | | —O—CH$_2$C(CH$_3$)$_2$NH$_2$ | —H |
| 4 | —NHC(=O)CH=CH— | | —O—CH$_3$ | —(CH$_2$)$_3$NH$_2$ |
| 5 | —NHC(=O)CH=CH— | | —O—(CH$_2$)$_2$NH$_2$ | —CF$_3$ |
| 6 | —NHC(=O)CH=CH— | | —O—(CH$_2$)$_3$NH$_2$ | —H |
| 7 | —NHC(=O)CH=CH— | | —O—(CH$_2$)$_2$O—(CH$_2$)$_2$—NH$_2$ | —H |
| 8 | —NHC(=O)CH=CH— | | —O—(CH$_2$)$_2$-morpholin-4-yl | —H |
| 9 | —NHC(=O)CH=CH— | | —O—(CH$_2$)$_2$-piperazin-4-yl | —H |
| 10 | —NHC(=O)CH=CH— | | —O—CH$_3$ | —(CH$_2$)$_2$N(CH$_3$)$_2$ |
| 11 | —NHC(=O)CH=CH— | | —H | 4-chlorophenyl |
| 12 | —NHC(=O)CH=CH— | | —H | 4-methoxyphenyl |
| 13 | —NHC(=O)CH=CH— | | —H | 3-cyanophenyl |
| 14 | —NHC(=O)CH=CH— | | morpholin-4-yl | —H |

TABLE A-continued

[Structure with OH, HO, R¹, R², R⁵, R⁶ substituents]

| Ex. | R¹ | R² | R⁵ | R⁶ |
|---|---|---|---|---|
| 15 | —NHC(=O)CH=CH— | | —O—CH₃ | 2-amino-3-ethyl-phenyl |
| 16 | —NHC(=O)CH=CH— | | —O—CH₃ | 1-morpholin-4-yl-methylene |
| 17 | —NHCHO | H | —H | phenyl |
| 18 | —NHCHO | H | —O—(CH₂)₂NH₂ | —H |
| 19 | —NHCHO | H | —O—CH₃ | —(CH₂)₂N(CH₃)₂ |
| 20 | —CH₂OH | H | —H | phenyl |
| 21 | —CH₂OH | H | —O—CH₃ | 2-amino-3-ethyl-phenyl |
| 22 | —CH₂OH | H | morpholin-4-yl | —H |
| 23 | —NHC(=O)CH=CH— | | —O—CH₃ | 3-chlorophenyl |
| 24 | —NHC(=O)CH=CH— | | —O—CH₃ | 3-cyanophenyl |
| 25 | —NHC(=O)CH=CH— | | —O—CH₃ | 3-aminomethyl-phenyl |
| 26 | —NHC(=O)CH=CH— | | —O—CH₃ | 4-aminomethyl-phenyl |
| 27 | —NHCHO | H | —O—CH₃ | 3-chlorophenyl |
| 28 | —NHCHO | H | —O—CH₃ | 3-cyanophenyl |
| 29 | —NHCHO | H | —O—CH₃ | 3-aminomethyl-phenyl |
| 30 | —NHCHO | H | —O—CH₃ | 4-aminomethyl-phenyl |
| 31 | —CH₂OH | H | —O—CH₃ | 3-chlorophenyl |
| 32 | —CH₂OH | H | —O—CH₃ | 3-cyanophenyl |
| 33 | —CH₂OH | H | —O—CH₃ | 3-aminomethyl-phenyl |
| 34 | —CH₂OH | H | —O—CH₃ | 4-aminomethyl-phenyl |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method of ameliorating, suppressing or alleviating the symptoms of asthma or chronic obstructive pulmonary in a mammal, the method comprising administering to the mammal a pharmaceutical composition comprising a pharmaceutically-acceptable carrier and a compound of formula (I):

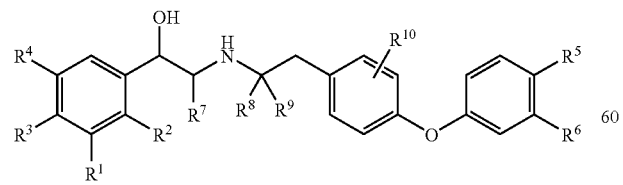

(I)

wherein:
each of $R^1$, $R^2$, $R^3$, and $R^4$ is independently selected from hydrogen, hydroxy, amino, halo, —CH₂OH and —NH-CHO, or $R^1$ and $R^2$ taken together are selected from —NHC(=O)CH=CH—, and —CH=CHC(=O)NH—;

$R^5$ and $R^6$ are independently selected from hydrogen, hydroxy, halo, $C_{1-6}$alkoxy, $C_{1-6}$alkyl, —$C_{1-6}$alkylenyl-$NR^aR^b$, —O—$C_{1-6}$alkylenyl-$NR^aR^b$; —O—$C_{1-4}$alkylenyl-O—$C_{1-4}$alkylenyl-$NR^aR^b$, —$SO_2NR^aR^b$, —$NR^cR^d$, phenyl, and heteroaryl; provided that $R^5$ and $R^6$ are not both hydrogen; wherein each phenyl is optionally substituted with 1 or 2 substituents selected from $R^f$; each heteroaryl is optionally substituted with 1 or 2 substituents selected from $R^g$; and each $C_{1-6}$alkyl is optionally substituted with 1 to 3 substituents selected from halo, hydroxy, $C_{1-6}$alkoxy, and amino;

$R^7$ is hydrogen or $C_{1-6}$alkyl;

$R^8$ is hydrogen or $C_{1-6}$alkyl;

$R^9$ is hydrogen or $C_{1-6}$alkyl;

$R^{10}$ is selected from hydrogen, halo, hydroxy, $C_{1-6}$alkyl, $C_{2-6}$alkenyl, $C_{2-6}$alkynyl, $C_{1-6}$alkoxy, aryl, heteroaryl, cycloalkyl, and heterocyclyl; or $R^9$ together with $R^{10}$ is —CH₂— or —CH₂CH₂—;

$R^a$, $R^b$, $R^c$, $R^d$, and $R^e$ are each independently hydrogen or $C_{1-6}$ alkyl, wherein each $C_{1-6}$alkyl is optionally substituted with 1 to 3 substituents selected from hydroxy, $C_{1-6}$alkoxy, and amino; or $R^a$ and $R^b$, or $R^c$ and $R^d$ together with the nitrogen atom to which they are attached form a heteroaryl or heterocyclic ring having from 4 to 7 ring atoms, and containing 1 to 3 heteroatoms selected from nitrogen, oxygen, and sulfur;

$R^f$ is selected from hydroxy, halo, $C_{1-6}$alkoxy, $C_{1-6}$alkyl, $C_{2-6}$alkenyl, $C_{2-6}$alkynyl, —C(=O)OH, —CN, —NO₂, —C(=O)$R^e$, —$SO_2$—$C_{1-6}$alkyl, —$C_{1-6}$alkylenyl-$NR^aR^b$, and —C(=O)$NR^aR^b$, wherein each $C_{1-6}$alkyl is optionally substituted with 1 to 3 substituents selected from halo, hydroxy, $C_{1-6}$alkoxy, and amino; and R$^g$ is C$_{1-6}$alkyl or oxo, wherein each C$_{1-6}$alkyl is optionally substituted with 1 to 3 substituents selected from halo, hydroxy, C$_{1-6}$alkoxy, and amino;

or a pharmaceutically-acceptable salt or stereoisomer thereof.

2. The method of claim 1 wherein the compound of formula (I) is a compound of formula (II):

(II)

[Chemical structure diagram showing a compound with OH, HO, R$^1$, R$^2$, NH, O, R$^5$, R$^6$ groups]

wherein:
R$^1$ is —CH$_2$OH or —NHCHO, and R$^2$ is hydrogen; or R$^1$ and R$^2$ taken together are —NHC(=O)CH=CH—, or —CH=CHC(=O)NH—;

R$^5$ and R$^6$ are each independently selected from hydrogen, hydroxy, C$_{1-6}$alkoxy, C$_{1-6}$alkyl, —C$_{1-6}$alkylenyl-NR$^a$R$^b$, —O—C$_{1-6}$alkylenyl-NR$^a$R$^b$; —NR$^c$R$^d$, phenyl, and heteroaryl; provided that R$^5$ and R$^6$ are not both hydrogen; wherein each phenyl is optionally substituted with 1 or 2 substituents selected from R$^f$; each heteroaryl is optionally substituted with 1 or 2 substituents selected from R$^g$; and each C$_{1-6}$alkyl is optionally substituted with 1 to 3 substituents selected from halo, hydroxy, C$_{1-6}$alkoxy, and amino;

R$^a$, R$^b$, R$^c$, R$^d$, and R$^e$ are each independently hydrogen or C$_{1-6}$ alkyl, wherein each C$_{1-6}$alkyl is optionally substituted with 1 to 3 substituents selected from hydroxy, C$_{1-6}$alkoxy, and amino; or R$^a$ and R$^b$, or R$^c$ and R$^d$ together with the nitrogen atom to which they are attached form a heteroaryl or heterocyclic ring having from 4 to 7 ring atoms, and containing 1 to 3 heteroatoms selected from nitrogen, oxygen, and sulfur;

R$^f$ is selected from hydroxy, halo, C$_{1-6}$alkoxy, C$_{1-6}$alkyl, —C(=O)OH, —CN, —NO$_2$, —C(=O)R$^e$, —C$_{1-6}$alkylenyl-NR$^a$R$^b$, and —C(=O)NR$^a$R$^b$; wherein each C$_{1-6}$alkyl is optionally substituted with 1 to 3 substituents selected from halo, hydroxy, C$_{1-6}$alkoxy, and amino; and R$^g$ is selected from C$_{1-6}$alkyl, wherein each C$_{1-6}$alkyl is optionally substituted with 1 to 3 substituents selected from halo, hydroxy, C$_{1-6}$alkoxy, and amino;

or a pharmaceutically-acceptable salt or stereoisomer thereof.

3. The method of claim 2, wherein R$^1$ is —CH$_2$OH, and R$^2$ is hydrogen.

4. The method of claim 2, wherein R$^1$ is —NHCHO, and R$^2$ is hydrogen.

5. The method of claim 2, wherein R$^1$ and R$^2$ taken together are —NHC(=O)CH=CH—, or —CH=CHC(=O)NH—.

6. The method of claim 2, wherein R$^5$ and R$^6$ are each independently selected from hydrogen, hydroxy, C$_{1-6}$alkoxy, C$_{1-6}$alkyl, —C$_{1-6}$alkylenyl NR$^a$R$^b$, —O—C$_{1-6}$alkylenyl-NR$^a$R$^b$, and —NR$^c$R$^d$; wherein for R$^5$ and R$^6$ each C$_{1-6}$alkyl is optionally substituted with 1 to 3 substituents selected from halo, hydroxy, C$_{1-6}$alkoxy, and amino.

7. The method of claim 2, wherein:
one of R$^5$ and R$^6$ is selected from —O(CH$_2$)$_2$NH$_2$, —O(CH$_2$)$_3$NH$_2$, —OCH$_2$C(CH$_3$)$_2$NH$_2$, —O(CH$_2$)$_4$NH$_2$, —(CH$_2$)$_2$NH$_2$, —(CH$_2$)$_3$NH$_2$, —CH$_2$C(CH$_3$)$_2$NH$_2$, —(CH$_2$)$_2$N(CH$_3$)$_2$, 4-morpholinylethoxy, and 4-piperazinylethoxy;

and the other of R$^5$ and R$^6$ is selected from hydrogen, methoxy, ethoxy, —CF$_3$, and methyl.

8. The method of claim 2, wherein:
R$^5$ is selected from hydrogen, hydroxy, methoxy, ethoxy, methyl, and ethyl; and R$^6$ is selected from phenyl, furyl, thienyl, pyrrolyl, and pyridyl; wherein phenyl is optionally substituted with 1 or 2 substituents selected from R$^f$; and furyl, thienyl, pyrrolyl, and pyridyl are optionally substituted with 1 or 2 substituents selected from R$^g$.

9. The method of claim 2, wherein
R$^5$ is hydrogen, methoxy or ethoxy;
and R$^6$ is phenyl optionally substituted with 1 or 2 substituents selected from R$^f$.

10. The method of claim 1, wherein the compound of formula (I) is selected from:

8-hydroxy-5-((R)-1-hydroxy-2-{2-[4-(6-methoxybiphenyl-3-yloxy)phenyl]-ethylamino}ethyl)-1H-quinolin-2-one;

5-((R)-2-{2-[4-(biphenyl-3-yloxy)phenyl]ethylamino}-1-hydroxyethyl)-8-hydroxy-1H-quinolin-2-one;

5-[(R)-2-(2-{4-[4-(2-amino-2-methylpropoxy)phenoxy]phenyl}ethyl-amino)-1-hydroxyethyl]-8-hydroxy-1H-quinolin-2-one;

5-[(R)-2-(2-{4-[3-(3-aminopropyl)-4-methoxyphenoxy]phenyl}ethyl-amino)-1-hydroxyethyl]-8-hydroxy-1H-quinolin-2-one;

5-[(R)-2-(2-{4-[4-(2-aminoethoxy)-3-trifluoromethylphenoxy]phenyl]-ethylamino)-1-hydroxyethyl]-8-hydroxy-1H-quinolin-2-one;

5-[(R)-2-(2-{4-[4-(3-aminopropoxy)phenoxy]phenyl}ethylamino)-1-hydroxyethyl]-8-hydroxy-1H-quinolin-2-one;

5-{(R)-2-[2-(4-{4-[2-(2-aminoethoxy)ethoxy]phenoxy}phenyl)ethyl-amino]-1-hydroxyethyl}-8-hydroxy-1H-quinolin-2-one;

8-hydroxy-5-[(R)-1-hydroxy-2-(2-{4-[4-(2-morpholin-4-ylethoxy)-phenoxy]phenyl}ethylamino)ethyl]-1H-quinolin-2-one;

8-hydroxy-5-[(R)-1-hydroxy-2-(2-{4-[4-(2-piperazin-1-ylethoxy)phenoxy]-phenyl}ethylamino)ethyl]-1H-quinolin-2-one;

5-[(R)-2-(2-{4-[3-(2-dimethylaminoethyl)-4-methoxyphenoxy]phenyl}-ethylamino)-1-hydroxyethyl]-8-hydroxy-1H-quinolin-2-one;

5-((R)-2-{2-[4-(4'-chlorobiphenyl-3-yloxy)phenyl]ethylamino}-1-hydroxyethyl)-8-hydroxy-1H-quinolin-2-one;

8-hydroxy-5-((R)-1-hydroxy-2-{2-[4-(4'-methoxybiphenyl-3-yloxy)-phenyl]ethylamino}ethyl)-1H-quinolin-2-one;

3'-(4-{2-[(R)-2-hydroxy-2-(8-hydroxy-2-oxo-1,2-dihydroquinolin-5-yl)ethylamino]ethyl}phenoxy)biphenyl-3-carbonitrile;

8-hydroxy-5-((R)-1-hydroxy-2-{2-[4-(4-morpholin-4-yl-phenoxy)-phenyl]ethylamino}ethyl)-1H-quinolin-2-one;

5-[(R)-2-(2-{4-[3'-(2-aminoethyl)-6-methoxybiphenyl-3-yloxy]phenyl}-ethylamino)-1-hydroxyethyl]-8-hydroxy-1H-quinolin-2-one;

8-hydroxy-5-((R)-1-hydroxy-2-{2-[4-(6-methoxy-3'-morpholin-4-ylmethylbiphenyl-3-yloxy)phenyl]ethylamino}ethyl)-1H-quinolin-2-one;

N-[5-((R)-2-{2-[4-(biphenyl-3-yloxy)phenyl]ethylamino}-1-hydroxyethyl)-2-hydroxyphenyl]formamide;
N-{5-[(R)-2-(2-{4-[4-(2-aminoethoxy)phenoxy]phenyl}ethylamino)-1-hydroxyethyl]-2-hydroxyphenyl}formamide;
N-{5-[(R)-2-(2-{4-[3-(2-dimethylaminoethyl)-4-methoxyphenoxy]phenyl}-ethylamino)-1-hydroxyethyl]-2-hydroxyphenyl}formamide;
4-((R)-2-{2-[4-(biphenyl-3-yloxy)phenyl]ethylamino}-1-hydroxyethyl)-2-hydroxymethylphenol;
4-((R)-2-{2-[4-(2'-amino-3'-ethyl-6-methoxybiphenyl-3-yloxy)phenyl]-ethylamino}-1-hydroxyethyl)-2-hydroxymethylphenol;
2-hydroxymethyl-4-((R)-1-hydroxy-2-{2-[4-(4-morpholin-4-ylphenoxy)-phenyl]ethylamino}ethyl)phenol;
5-(2-{2-[4-(3'-chloro-6-methoxybiphenyl-3-yloxy)phenyl]ethylamino}-1-hydroxyethyl)-8-hydroxy-1H-quinolin-2-one;
5'-(4-{2-[2-hydroxy-2-(8-hydroxy-2-oxo-1,2-dihydroquinolin-5-yl)ethyl-amino]ethyl}phenoxy)-2'-methoxybiphenyl-3-carbonitrile;
5-(2-{2-[4-(3'-aminomethyl-6-methoxybiphenyl-3-yloxy)phenyl]ethyl-amino}-1-hydroxyethyl)-8-hydroxy-1H-quinolin-2-one;
5-(2-{2-[4-(4'-aminomethyl-6-methoxybiphenyl-3-yloxy)phenyl]ethyl-amino}-1-hydroxyethyl)-8-hydroxy-1H-quinolin-2-one;
N-[5-(2-{2-[4-(3'-chloro-6-methoxybiphenyl-3-yloxy)phenyl]ethyl-amino}-1-hydroxyethyl)-2-hydroxyphenyl]formamide;
N-[5-(2-{2-[4-(3'-cyano-6-methoxybiphenyl-3-yloxy)phenyl]ethyl-amino}-1-hydroxyethyl)-2-hydroxyphenyl]formamide;
N-[5-(2-{2-[4-(3'-aminomethyl-6-methoxybiphenyl-3-yloxy)phenyl]-ethylamino}-1-hydroxyethyl)-2-hydroxyphenyl]formamide;
N-[5-(2-{2-[4-(4'-aminomethyl-6-methoxybiphenyl-3-yloxy)phenyl]-ethylamino}-1-hydroxyethyl)-2-hydroxyphenyl]formamide;
4-(2-{2-[4-(3'-chloro-6-methoxybiphenyl-3-yloxy)phenyl]ethylamino}-1-hydroxyethyl)-2-hydroxymethylphenol;
5'-(4-{2-[2-hydroxy-2-(4-hydroxy-3-hydroxymethylphenyl)ethylamino]-ethyl}phenoxy)-2'-methoxybiphenyl-3-carbonitrile;
4-(2-{2-[4-(3'-aminomethyl-6-methoxybiphenyl-3-yloxy)phenyl]ethyl-amino}-1-hydroxyethyl)-2-hydroxymethylphenol; and
4-(2-{2-[4-(4'-aminomethyl-6-methoxybiphenyl-3-yloxy)phenyl]ethyl-amino}-1-hydroxyethyl)-2-hydroxymethylphenol; and
pharmaceutically acceptable salts thereof.

11. The method of claim 1 wherein the pharmaceutical composition is administered by inhalation.

12. The method of claim 10 wherein the pharmaceutical composition is administered by inhalation.

13. The method of claim 1 wherein the method further comprises administering one or more other therapeutic agents.

14. The method of claim 13 wherein the other therapeutic agent is a corticosteroid.

15. The method of claim 10 wherein the method further comprises administering one or more other therapeutic agents.

16. The method of claim 15 wherein the other therapeutic agent is a corticosteroid.

* * * * *